US010159544B2

United States Patent
Damon

(10) Patent No.: US 10,159,544 B2
(45) Date of Patent: *Dec. 25, 2018

(54) ORTHODONTIC BRACKET

(71) Applicant: Ormco Corporation, Orange, CA (US)

(72) Inventor: Dwight H. Damon, Spokane, WA (US)

(73) Assignee: Ormco Corporation, Orange, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/879,089

(22) Filed: Jan. 24, 2018

(65) Prior Publication Data

US 2018/0161127 A1 Jun. 14, 2018

Related U.S. Application Data

(60) Continuation of application No. 14/971,012, filed on Dec. 16, 2015, now Pat. No. 9,895,207, which is a continuation of application No. 12/755,054, filed on Apr. 6, 2010, now Pat. No. 9,277,973, which is a division of application No. 11/408,873, filed on Apr. 19, 2006, now Pat. No. 7,704,072.

(51) Int. Cl.
*A61C 7/28* (2006.01)

(52) U.S. Cl.
CPC .................... *A61C 7/287* (2013.01)

(58) Field of Classification Search
CPC .............. A61C 7/12; A61C 7/14; A61C 7/287
See application file for complete search history.

(56) References Cited

U.S. PATENT DOCUMENTS

| 550,508 A | 11/1895 | Woodbury |
| 1,166,766 A | 1/1916 | Kelsey |
| 2,046,414 A * | 7/1936 | Russell ............... A61C 7/00 433/13 |
| 2,549,528 A | 4/1951 | Russell |
| 2,602,998 A | 7/1952 | Sprague |
| 2,671,964 A | 3/1954 | Russell et al. |
| 2,686,365 A | 8/1954 | Schurter |

(Continued)

FOREIGN PATENT DOCUMENTS

| EP | 0 623 320 A1 | 11/1994 |
| EP | 1508310 A2 | 2/2005 |

(Continued)

OTHER PUBLICATIONS

Ralph A. Lewis; Office Action issued in U.S. Appl. No. 12/147,877; dated Nov. 24, 2010; 23 pages; U.S. Patent and Trademark Office.

(Continued)

*Primary Examiner* — Heidi M Eide
(74) *Attorney, Agent, or Firm* — Wood Herron & Evans LLP

(57) ABSTRACT

An orthodontic bracket is described and which includes a base member defining an archwire slot having an opening, and at least one projection extending outwardly from the base member; a ligating slide moveable between a first position which is clear of the archwire slot, and second position where the ligating slide projects over the opening of the archwire slot; and a biasing member borne by the ligating slide, and resiliently cooperating with the projection, and wherein the biasing member has a first portion which receives the projection when the ligating slide is in the first position, and a second portion which receives the projection when the ligating slide is in the second position.

18 Claims, 24 Drawing Sheets

(56) References Cited

U.S. PATENT DOCUMENTS

| | | |
|---|---|---|
| 3,087,244 A | 4/1963 | Huettner et al. |
| 3,438,132 A | 4/1969 | Rubin |
| 3,748,740 A | 7/1973 | Wildman |
| 3,750,288 A | 8/1973 | Culbreth |
| 3,772,787 A | 11/1973 | Hanson |
| 3,780,437 A | 12/1973 | Wildman |
| 3,871,098 A | 3/1975 | Dean |
| 3,946,488 A | 3/1976 | Miller et al. |
| RE28,889 E | 7/1976 | Wildman |
| 4,001,940 A | 1/1977 | Cusato |
| 4,035,919 A | 7/1977 | Cusato |
| 4,077,126 A | 3/1978 | Pletcher |
| 4,144,642 A | 3/1979 | Wallshein |
| 4,196,517 A | 4/1980 | Forster |
| 4,209,906 A | 7/1980 | Fujita |
| 4,229,166 A | 10/1980 | Cusato et al. |
| 4,248,588 A | 2/1981 | Hanson |
| 4,277,236 A | 7/1981 | Kurz |
| 4,323,347 A | 4/1982 | Weissman |
| 4,355,975 A | 10/1982 | Fujita |
| 4,371,337 A | 2/1983 | Pletcher |
| 4,419,078 A | 12/1983 | Pletcher |
| 4,443,189 A | 4/1984 | Wildman |
| 4,449,933 A | 5/1984 | Forni |
| 4,455,138 A | 6/1984 | Sheridan |
| 4,465,461 A | 8/1984 | Schutz |
| 4,559,012 A | 12/1985 | Pletcher |
| 4,655,708 A | 4/1987 | Fujita |
| 4,696,646 A | 9/1987 | Maitland |
| 4,698,017 A | 10/1987 | Hanson |
| 4,708,651 A | 11/1987 | Buchanan |
| 4,747,777 A | 5/1988 | Ward |
| 4,768,950 A | 9/1988 | Armstrong et al. |
| 4,799,882 A | 1/1989 | Kesling |
| 4,822,277 A | 4/1989 | Nevell |
| 4,875,855 A | 10/1989 | Beckett |
| 4,878,840 A | 11/1989 | Reynolds |
| 4,904,183 A | 2/1990 | Hannan et al. |
| 4,964,800 A | 10/1990 | Good |
| 5,028,234 A | 7/1991 | Schweitzer et al. |
| 5,039,302 A | 8/1991 | Keys |
| 5,094,614 A | 3/1992 | Wildman |
| 5,184,631 A | 2/1993 | Ikeda |
| 5,261,813 A | 11/1993 | Baker |
| 5,269,681 A | 12/1993 | Degnan |
| 5,275,557 A | 1/1994 | Damon |
| 5,295,831 A | 3/1994 | Patterson et al. |
| 5,295,886 A | 3/1994 | Wildman |
| 5,320,532 A | 6/1994 | Farzin-Nia et al. |
| 5,322,435 A * | 6/1994 | Pletcher ............... A61C 7/145 433/10 |
| 5,326,261 A | 7/1994 | Rains |
| 5,429,500 A | 7/1995 | Damon |
| 5,439,378 A | 8/1995 | Damon |
| 5,466,151 A | 11/1995 | Damon |
| 5,474,444 A | 12/1995 | Wildman |
| 5,474,445 A | 12/1995 | Voudouris |
| 5,474,446 A | 12/1995 | Wildman et al. |
| 5,511,976 A | 4/1996 | Wildman |
| 5,607,299 A | 3/1997 | Nicholson |
| 5,630,715 A | 5/1997 | Voudouris |
| 5,630,716 A | 5/1997 | Hanson |
| 5,711,666 A | 1/1998 | Hanson |
| 5,743,737 A | 4/1998 | Hawn et al. |
| 5,791,897 A | 8/1998 | Wildman |
| 5,857,849 A | 1/1999 | Kurz |
| 5,857,850 A | 1/1999 | Voudouris |
| 5,863,198 A | 1/1999 | Doyle |
| 5,863,199 A | 1/1999 | Wildman |
| 5,873,716 A | 2/1999 | Kesling |
| 5,890,893 A | 4/1999 | Heiser |
| 5,906,486 A | 5/1999 | Hanson |
| 5,908,293 A | 6/1999 | Voudouris |
| 5,913,680 A | 6/1999 | Voudouris |
| 5,971,753 A | 10/1999 | Heiser |
| 6,071,118 A | 6/2000 | Damon |
| 6,071,119 A | 6/2000 | Christoff et al. |
| 6,168,428 B1 | 1/2001 | Voudouris |
| 6,174,162 B1 | 1/2001 | Pozzi |
| 6,190,166 B1 | 2/2001 | Sasakura |
| 6,193,508 B1 | 2/2001 | Georgakis |
| 6,247,923 B1 | 6/2001 | Vashi |
| 6,296,482 B1 | 10/2001 | Kapit |
| 6,319,004 B1 | 11/2001 | Forsline |
| 6,368,105 B1 | 4/2002 | Voudouris et al. |
| 6,375,458 B1 | 4/2002 | Moorleghem et al. |
| 6,428,314 B1 | 8/2002 | Jones, Jr. et al. |
| 6,485,299 B1 | 11/2002 | Wildman |
| 6,506,049 B2 | 1/2003 | Hanson |
| 6,582,226 B2 | 6/2003 | Jordan et al. |
| 6,632,088 B2 | 10/2003 | Voudouris |
| 6,659,767 B2 | 12/2003 | Abels et al. |
| 6,659,769 B2 | 12/2003 | Flanagan |
| 6,701,939 B2 | 3/2004 | Freeman |
| 6,726,474 B2 | 4/2004 | Spencer |
| 6,786,718 B2 | 9/2004 | Lauren et al. |
| 6,796,797 B2 | 9/2004 | Muller et al. |
| 6,942,483 B2 | 9/2005 | Heiser |
| 6,994,548 B2 | 2/2006 | Perret, Jr. |
| 7,011,517 B2 | 3/2006 | Nicozisis |
| 7,104,791 B2 | 9/2006 | Hanson |
| 7,128,571 B2 | 10/2006 | Young |
| 7,214,056 B2 | 5/2007 | Stockstill |
| 7,255,557 B2 | 8/2007 | Forster |
| 7,267,545 B2 | 9/2007 | Oda |
| 7,335,020 B2 | 2/2008 | Castner et al. |
| 7,416,408 B2 | 8/2008 | Farzin-Nia et al. |
| 7,419,375 B2 | 9/2008 | Farzin-Nia et al. |
| 7,442,039 B2 | 10/2008 | Opin et al. |
| 7,481,651 B2 | 1/2009 | Sernetz et al. |
| 7,621,743 B2 | 11/2009 | Bathen et al. |
| 7,704,072 B2 | 4/2010 | Damon |
| 7,963,767 B2 | 6/2011 | Lewis et al. |
| 8,029,276 B1 | 10/2011 | Lokar |
| 8,033,824 B2 | 10/2011 | Oda et al. |
| 9,277,973 B2 | 3/2016 | Damon |
| 9,895,207 B2 | 2/2018 | Damon |
| 2002/0006595 A1 | 1/2002 | Voudouris |
| 2003/0049582 A1 | 3/2003 | Abels |
| 2004/0166458 A1 | 8/2004 | Opin et al. |
| 2004/0265778 A1 | 12/2004 | Kliff et al. |
| 2005/0239012 A1* | 10/2005 | Bathen .................. A61C 7/287 433/10 |
| 2005/0244775 A1 | 11/2005 | Abels et al. |
| 2005/0277082 A1 | 12/2005 | Christoff |
| 2006/0063123 A1 | 3/2006 | Cleary et al. |
| 2006/0177790 A1 | 8/2006 | Farzin-Nia et al. |
| 2006/0228662 A1 | 10/2006 | Lokar |
| 2006/0263737 A1 | 11/2006 | Oda |
| 2007/0072143 A1 | 3/2007 | Sommer |
| 2007/0082315 A1 | 4/2007 | Sabater |
| 2007/0160949 A1 | 7/2007 | Voudouris |
| 2007/0178419 A1 | 8/2007 | Berman et al. |
| 2007/0178422 A1 | 8/2007 | Voudouris |
| 2007/0202460 A1 | 8/2007 | Chao |
| 2007/0224569 A1 | 9/2007 | Oda |
| 2007/0243497 A1* | 10/2007 | Voudouris .............. A61C 7/141 433/10 |
| 2007/0248928 A1 | 10/2007 | Damon |
| 2007/0259301 A1 | 11/2007 | Hagelganz et al. |
| 2007/0259304 A1 | 11/2007 | Hagelganz et al. |
| 2008/0113311 A1 | 5/2008 | Forster |
| 2009/0004619 A1 | 1/2009 | Oda et al. |
| 2009/0155734 A1 | 6/2009 | Damon |
| 2010/0178629 A1 | 7/2010 | Oda et al. |
| 2010/0196838 A1 | 8/2010 | Damon |
| 2011/0123942 A1 | 5/2011 | Rudman |

FOREIGN PATENT DOCUMENTS

| | | |
|---|---|---|
| JP | 5454495 | 4/1979 |
| JP | 2001503305 T | 3/2001 |
| JP | 2001104340 A | 4/2001 |

(56) References Cited

FOREIGN PATENT DOCUMENTS

| | | |
|---|---|---|
| JP | 2001269356 A | 10/2001 |
| JP | 2004188177 A | 7/2004 |
| JP | 2004255190 A | 9/2004 |
| JP | 2004526536 T | 9/2004 |
| JP | 2005502388 T | 1/2005 |
| WO | 94/23666 A1 | 10/1994 |
| WO | 0033760 A1 | 6/2000 |
| WO | 2005007011 A2 | 1/2005 |
| WO | 2009116560 A1 | 9/2009 |

OTHER PUBLICATIONS

European Patent Office, International Search Report and Written Opinion in PCT Application No. PCT/US2008/068545, dated Jan. 26, 2009.

U.S. Patent and Trademark Office, International Search Report and Written Opinion in PCT Application No. PCT/US2010/023718, dated Apr. 15, 2010.

U.S. Patent and Trademark Office, International Search Report and Written Opinion in PCT Application No. PCT/US2010/021153, dated Mar. 22, 2010.

Radial. (n.d.) Dictionary.com Unabridged. Retrieved Oct. 20, 2009, from Dictionary.com website: http://dictionary.reference.com/browse/radial.

http://www.classoneorthodontics.com, website, Feb. 9, 2009, 3 pgs.

European Patent Office, The International Bureau of WIPO, International Preliminary Report on Patentability in PCT Application No. PCT/US2008/068545, dated Jan. 5, 2010.

U.S. Patent and Trademark Office, Office Action in U.S. Appl. No. 11/408,873 dated May 15, 2009.

U.S. Patent and Trademark Office, Final Office Action in U.S. Appl. No. 11/408,873, dated Oct. 27, 2009.

U.S. Patent and Trademark Office, Office Action in U.S. Appl. No. 12/686,824, dated Dec. 16, 2011.

U.S. Patent and Trademark Office, Final Office Action in U.S. Appl. No. 12/686,824, dated Sep. 10, 2012.

U.S. Patent and Trademark Office, Notice of Allowance issued in U.S. Appl. No. 12/755,054 dated Jan. 14, 2016.

U.S. Patent and Trademark Office, final Office Action issued in U.S. Appl. No. 12/755,054 dated Sep. 21, 2015.

U.S. Patent and Trademark Office, Office Action issued in U.S. Appl. No. 12/755,054 dated Mar. 6, 2015.

U.S. Patent and Trademark Office, final Office Action issued in U.S. Appl. No. 12/755,054 dated Apr. 29, 2014.

U.S. Patent and Trademark Office, Office Action issued in U.S. Appl. No. 12/755,054 dated Nov. 12, 2013.

U.S. Patent and Trademark Office, final Office Action issued in U.S. Appl. No. 12/755,054 dated Mar. 25, 2013.

U.S. Patent and Trademark Office, Office Action issued in U.S. Appl. No. 12/755,054 dated Sep. 5, 2012.

European Patent Office, European Search Report issued in corresponding European Application No. EP08252175 dated Oct. 28, 2008.

U.S. Patent and Trademark Office, Official Action for corresponding U.S. Appl. No. 12/147,891, dated Dec. 10, 2010 5 pages).

USPTO, final Office Action issued in related U.S. Appl. No. 12/147,891, dated May 26, 2011.

USPTO, Office Action issued in related U.S. Appl. No. 12/147,891, dated Dec. 20, 2011.

Japanese Patent Office, Office Action issued in related Japanese Patent Application Serial No. 2008-169272, dated Apr. 19, 2011.

U.S. Patent and Trademark Office, Office Action in U.S. Appl. No. 12/147,854, dated Nov. 26, 2010.

U.S. Patent and Trademark Office, Office Action in U.S. Appl. No. 12/147,854, dated Jun. 29, 2011.

U.S. Patent and Trademark Office, final Office Action in U.S. Appl. No. 12/147,854, dated Feb. 3, 2012.

http://www.classoneorthodontics.com website (2 pages) Mar. 2, 2006.

U.S. Patent and Trademark Office, Office Action in U.S. Appl. No. 14/969,881, dated Jun. 10, 2016.

U.S. Patent and Trademark Office, Office Action in U.S. Appl. No. 14/968,065, dated Jun. 6, 2016.

U.S. Patent and Trademark Office, Office Action in U.S. Appl. No. 14/971,012 dated May 10, 2016.

U.S. Patent and Trademark Office, Final Office Action in U.S. Appl. No. 14/971,012 dated Oct. 14, 2016.

U.S. Patent and Trademark Office, Office Action in U.S. Appl. No. 14/971,012 dated May 16, 2017.

U.S. Patent and Trademark Office, Final Office Action in U.S. Appl. No. 14/971,012 dated Sep. 26, 2017.

U.S. Patent and Trademark Office, Notice of Allowance in U.S. Appl. No. 14/971,012 dated Dec. 6, 2017.

U.S. Patent and Trademark Office, Office Action in U.S. Appl. No. 14/969,881 dated Nov. 16, 2016.

U.S. Patent and Trademark Office, Office Action in U.S. Appl. No. 14/969,881 dated May 24, 2017.

U.S. Patent and Trademark Office, Notice of Allowance in U.S. Appl. No. 14/969,881 dated Oct. 27, 2017.

* cited by examiner

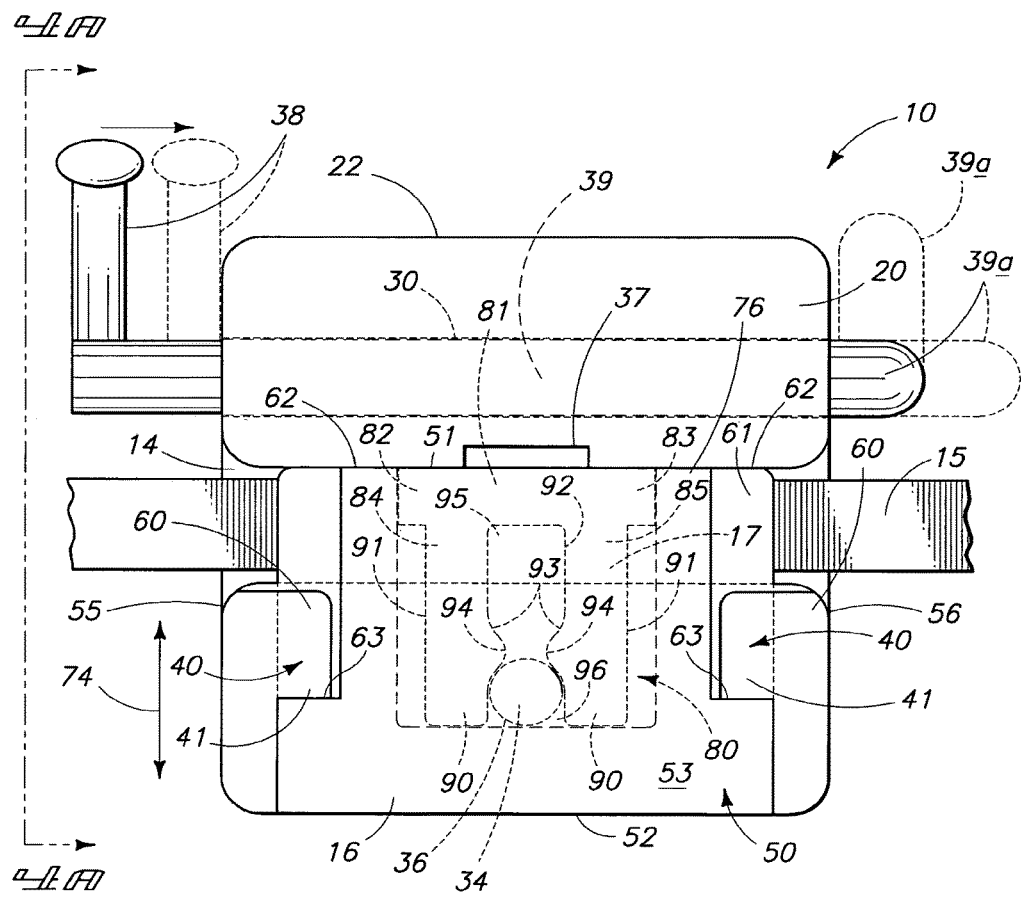

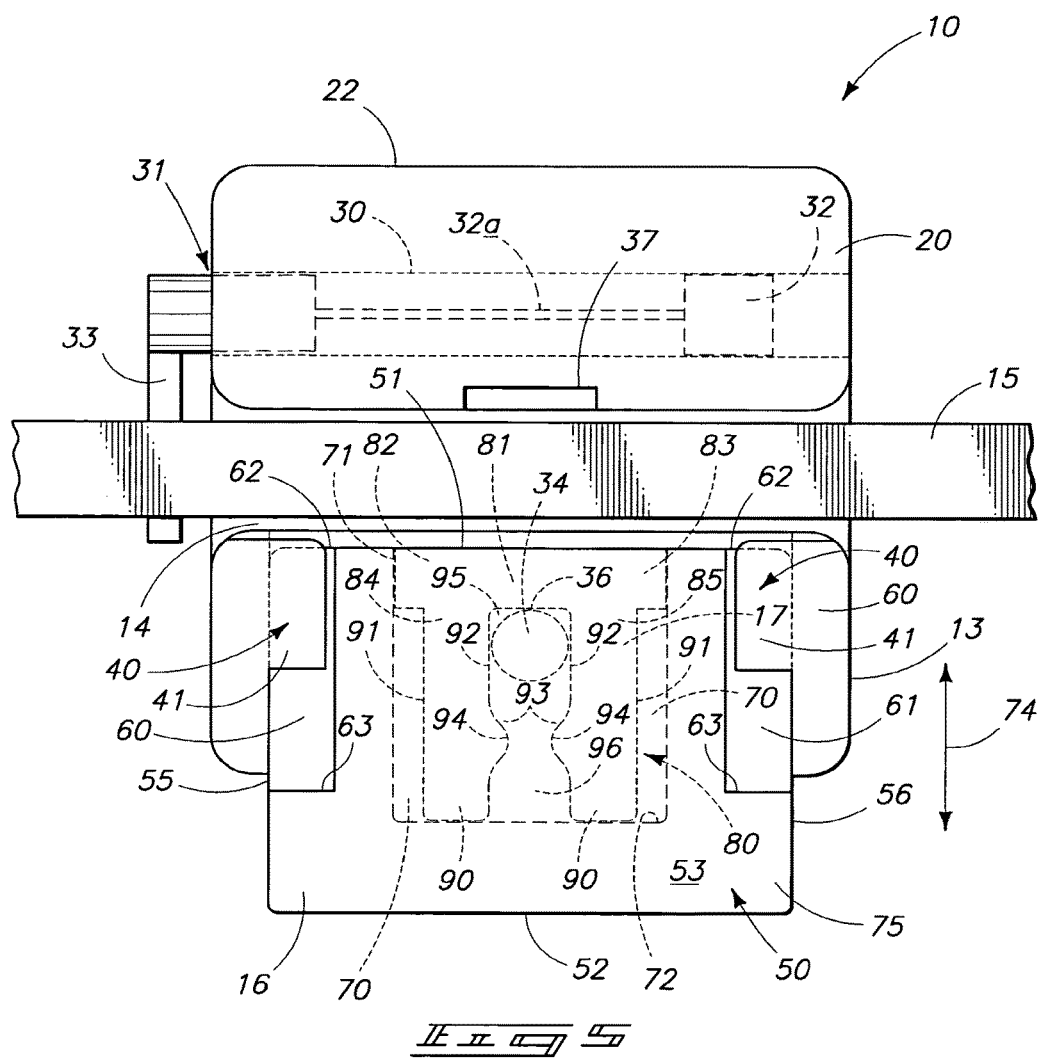

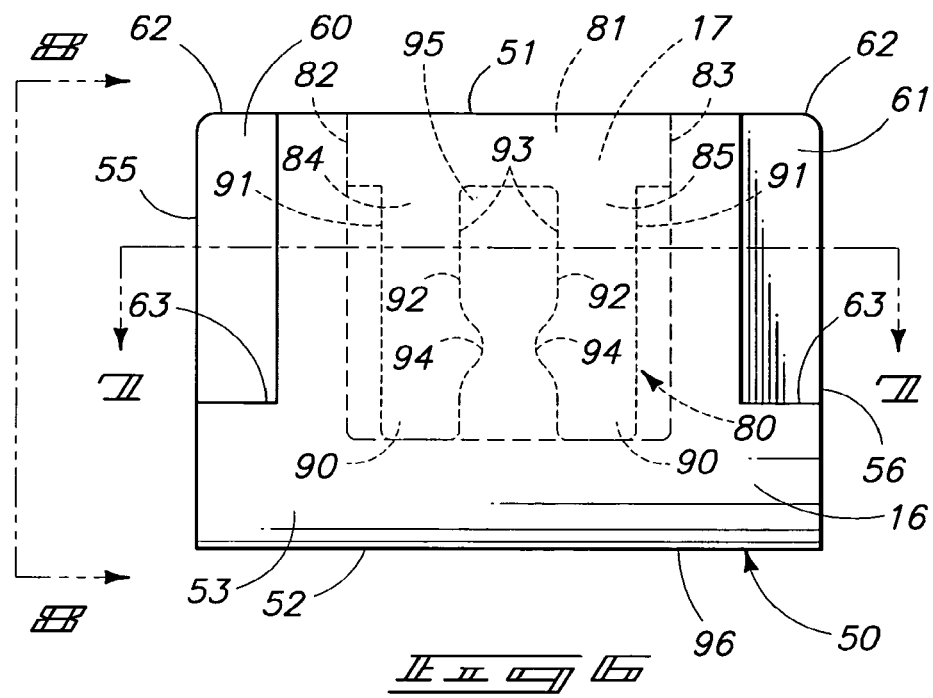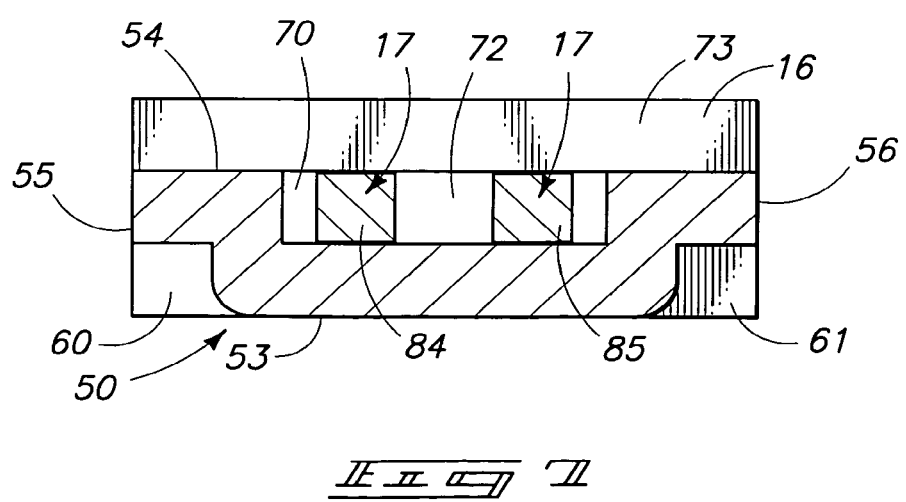

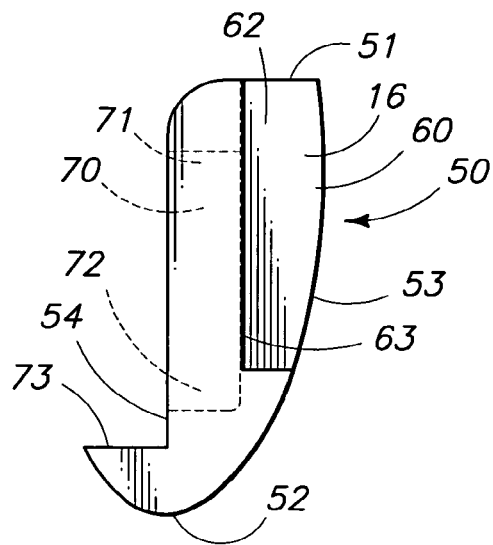
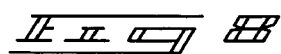
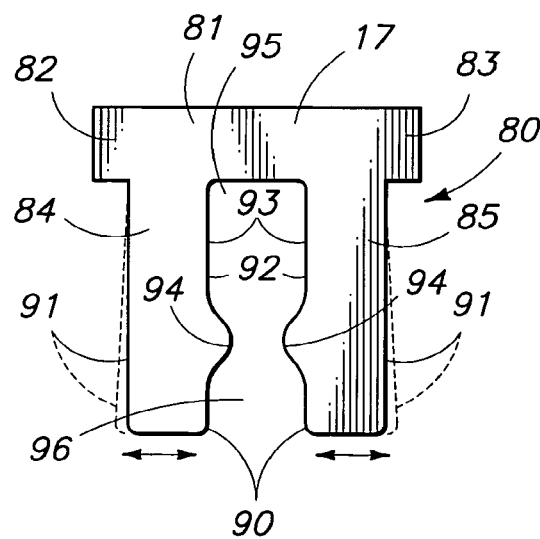
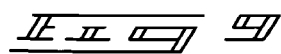

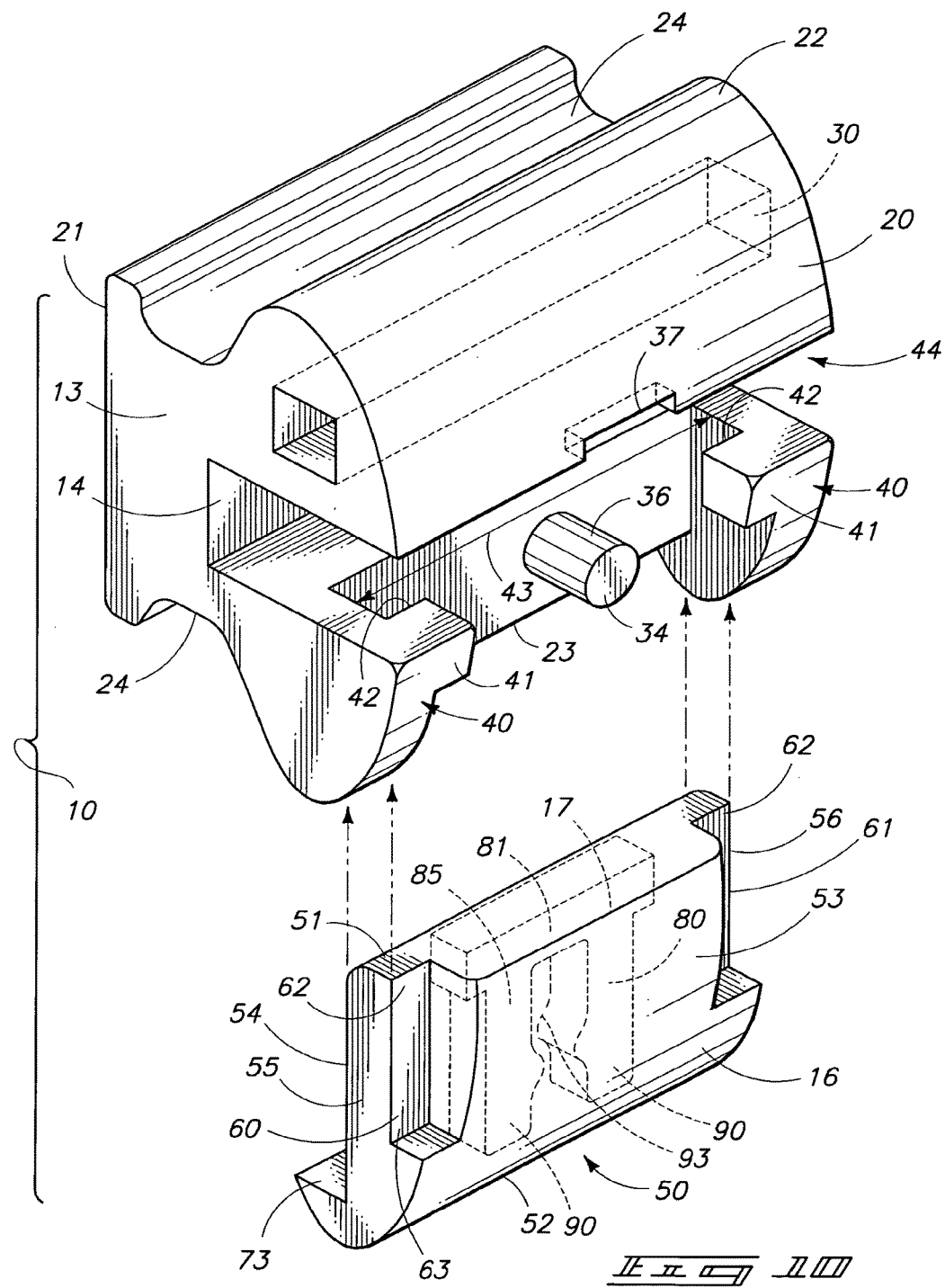

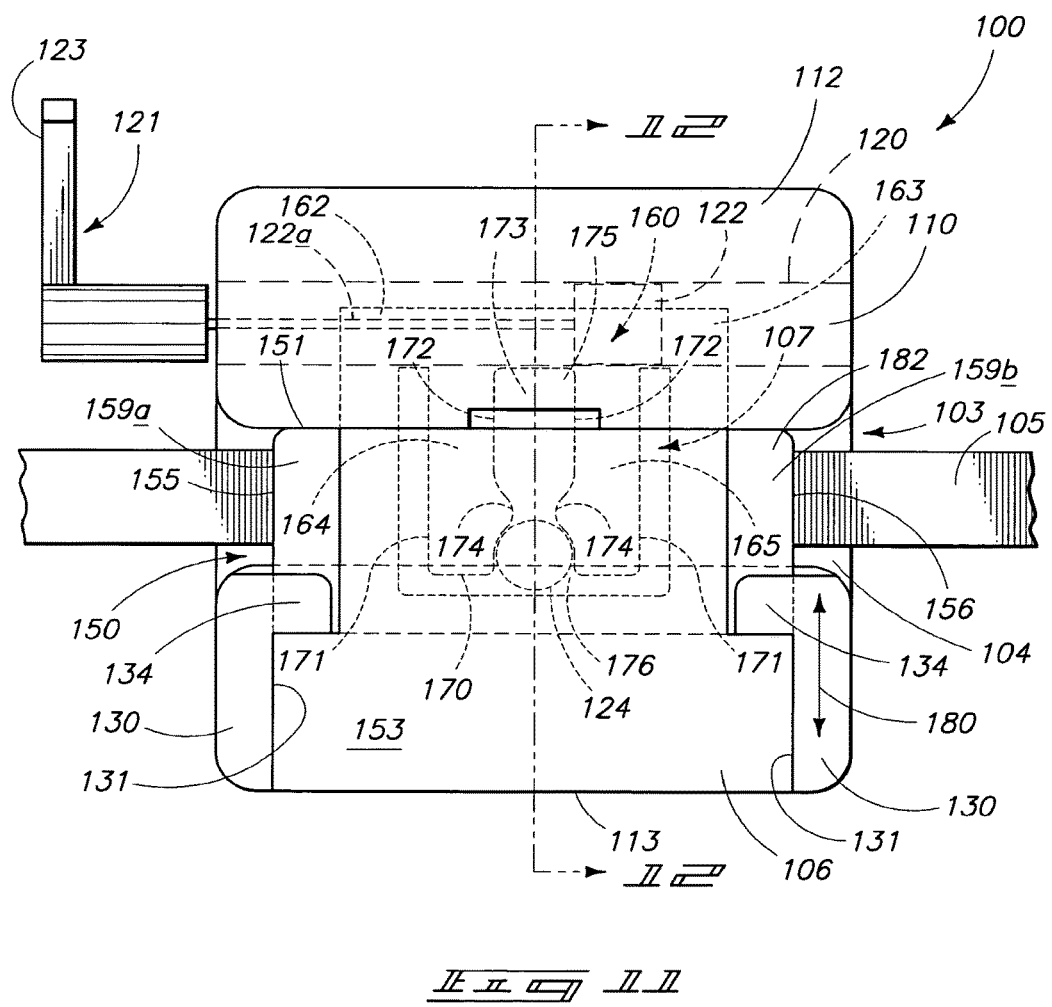

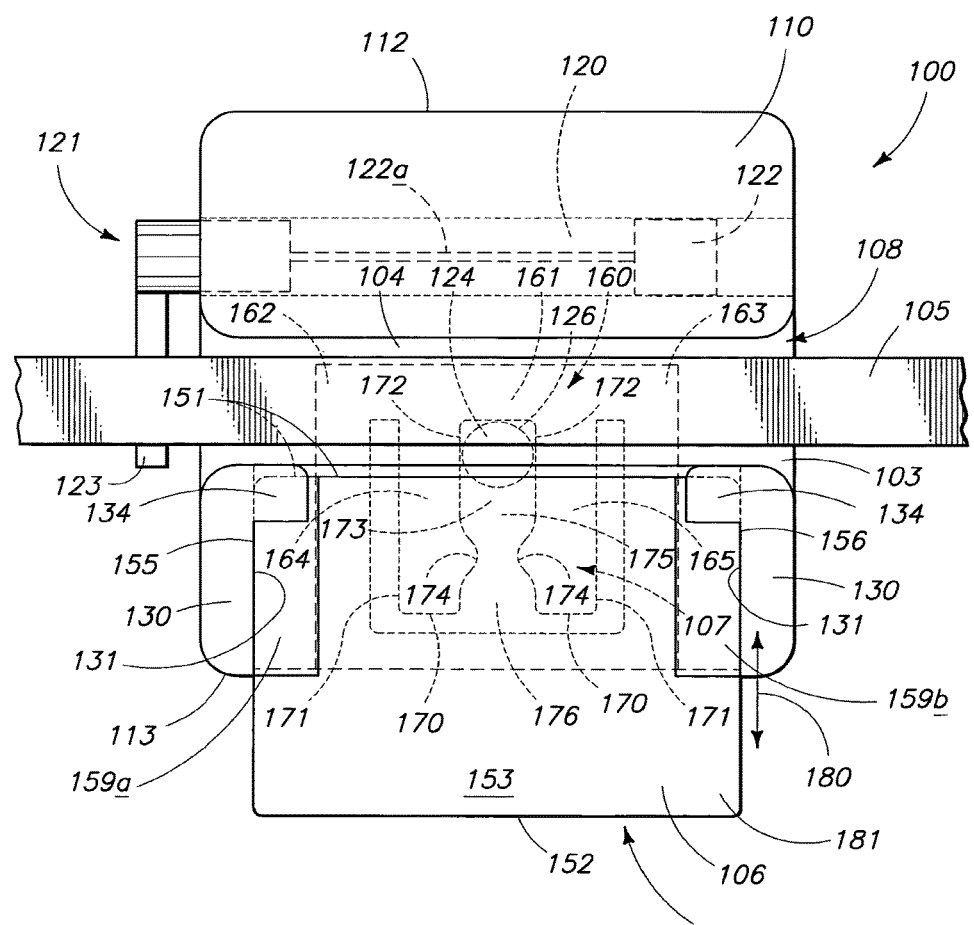

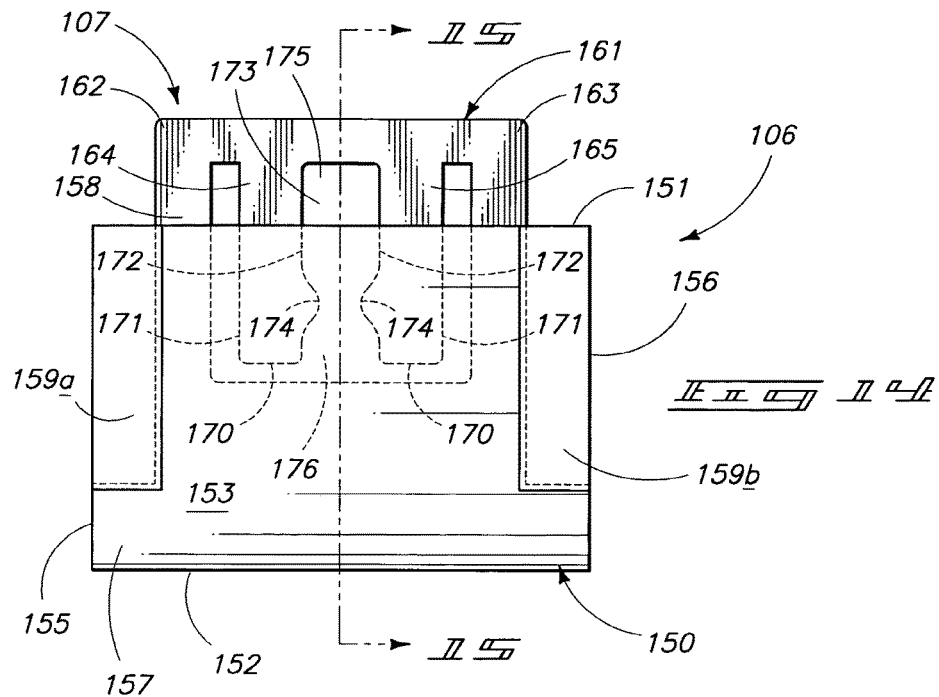
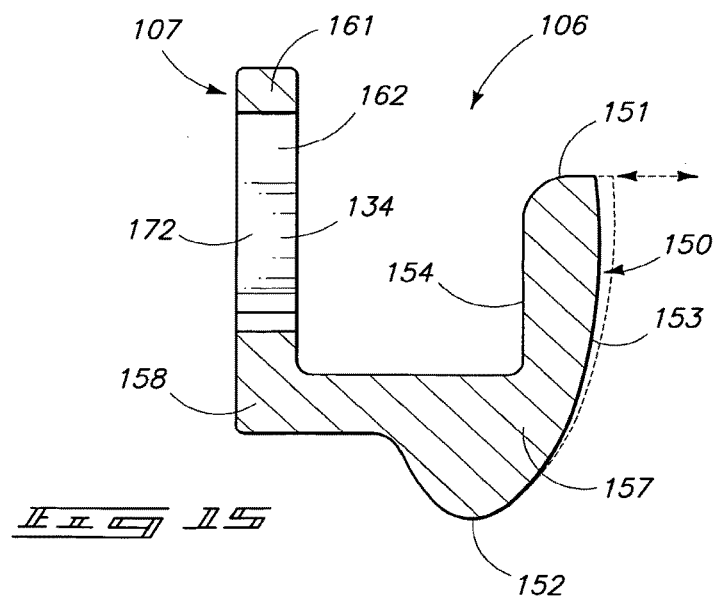

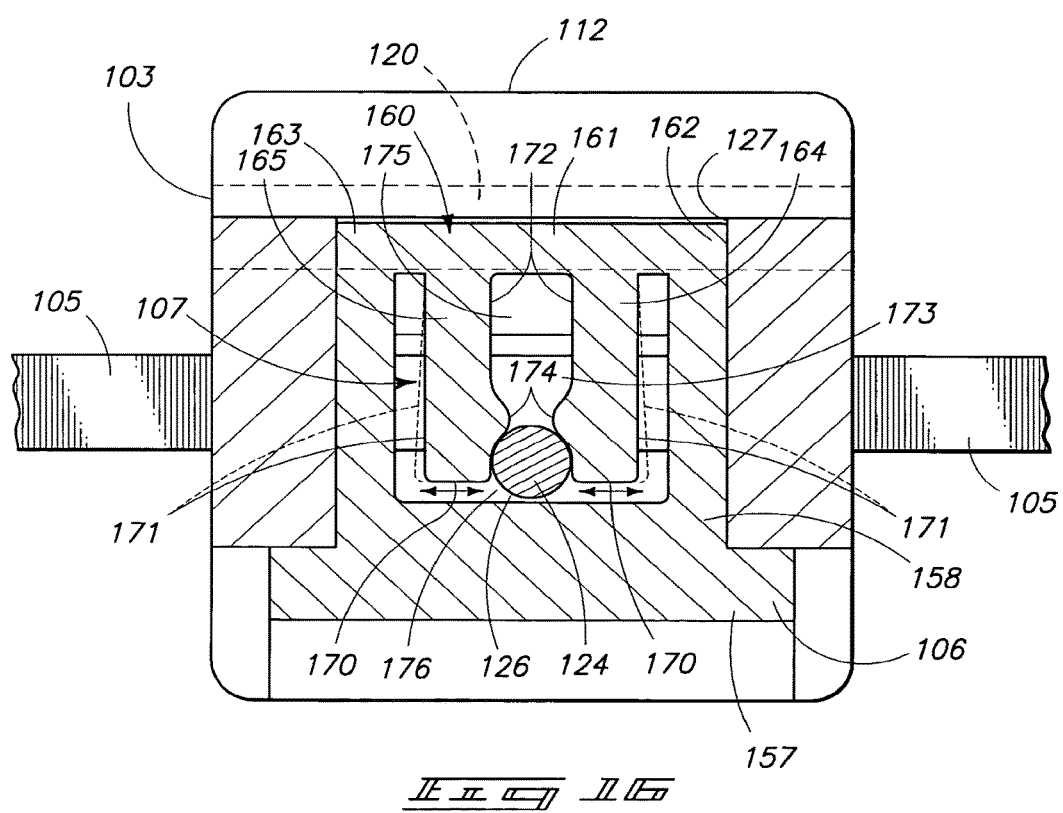

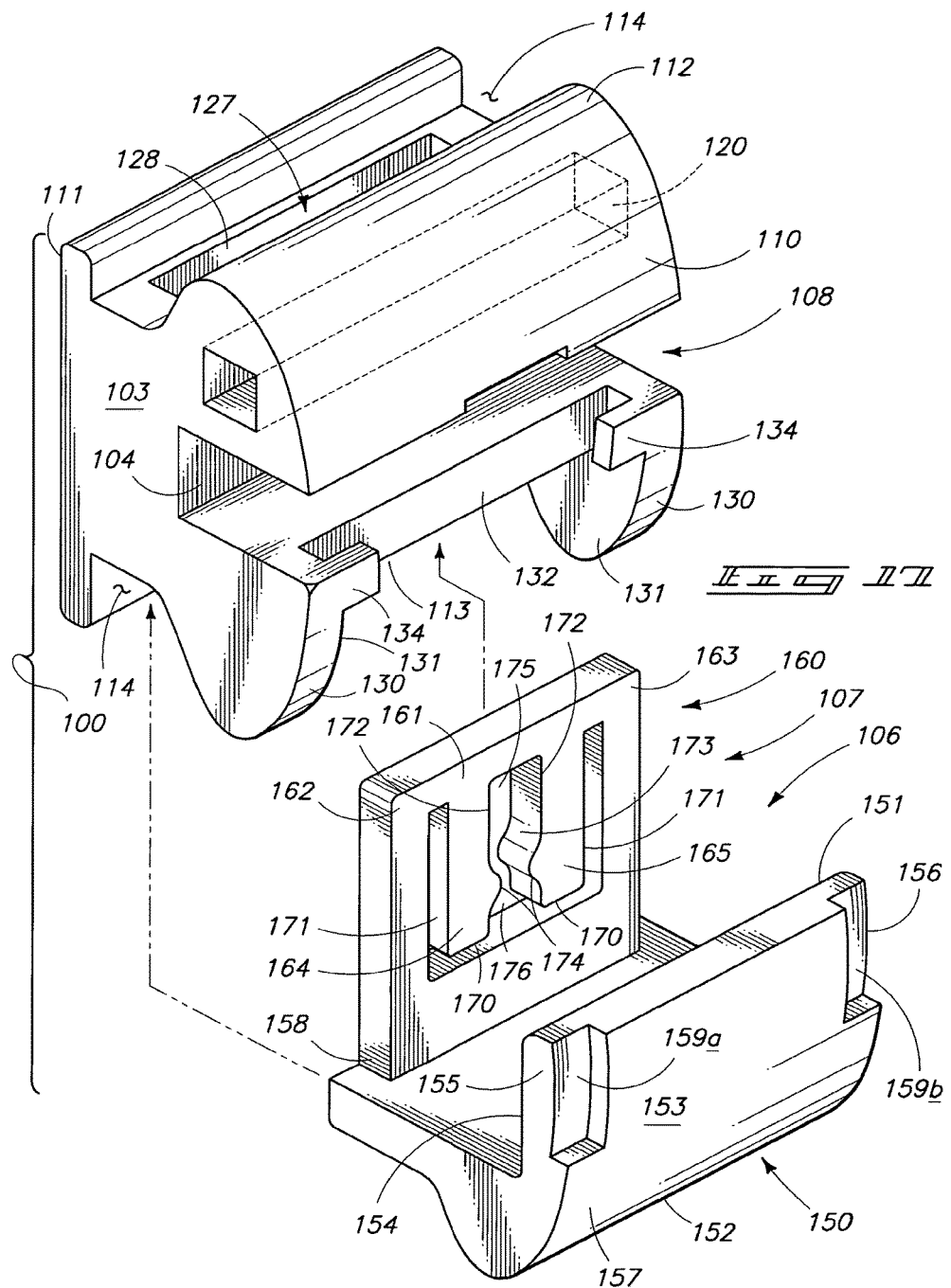

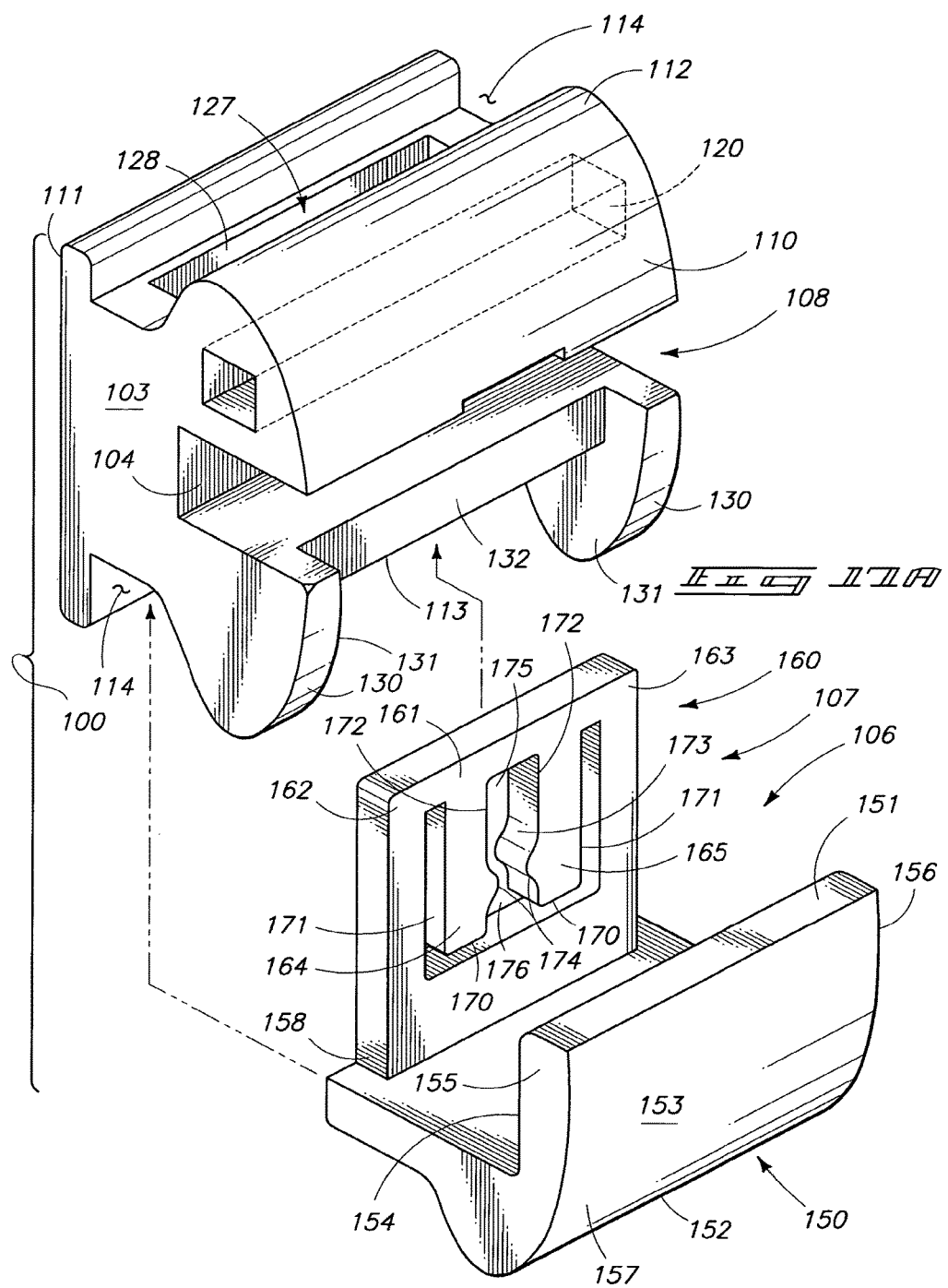

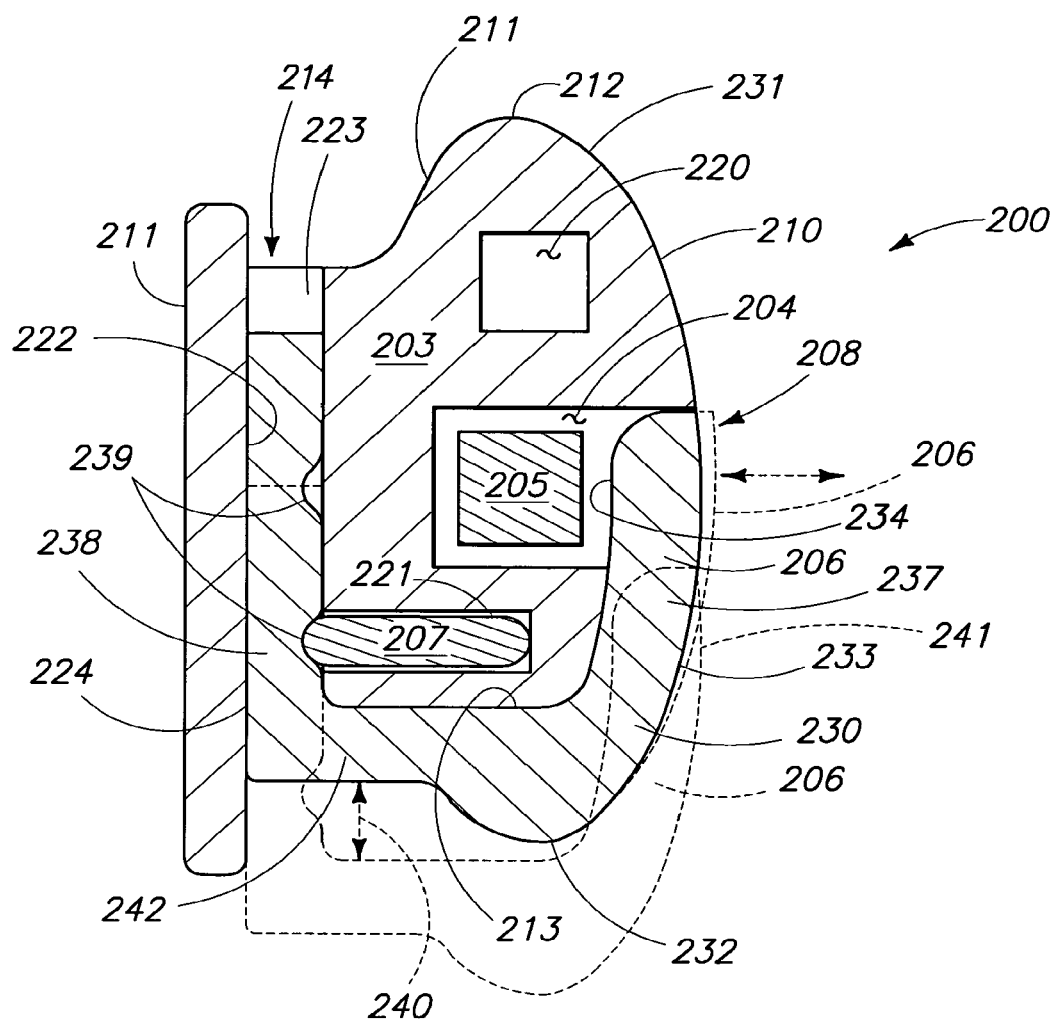

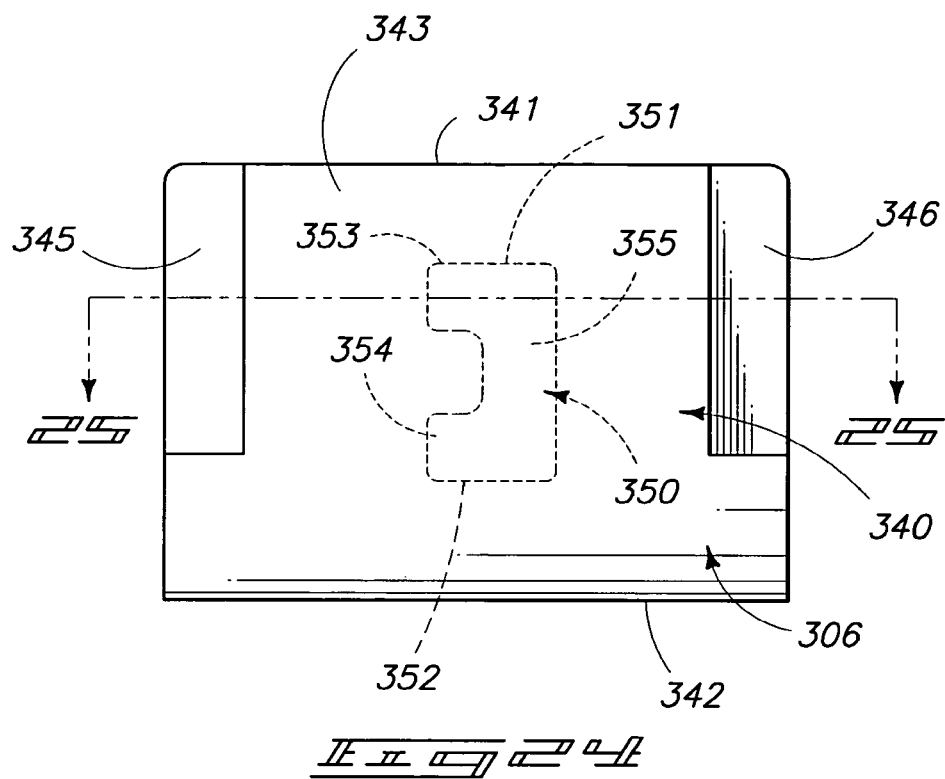
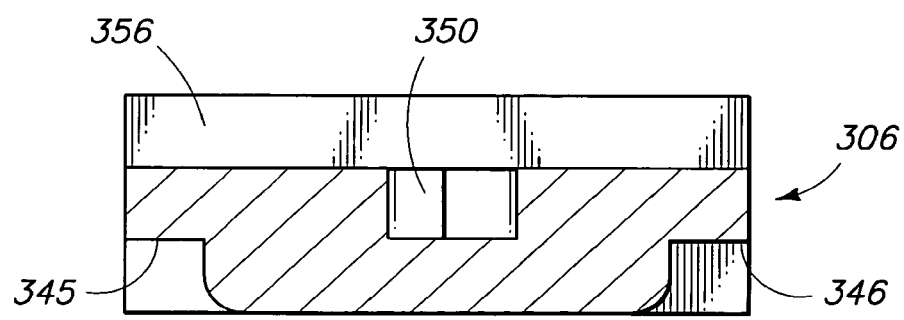

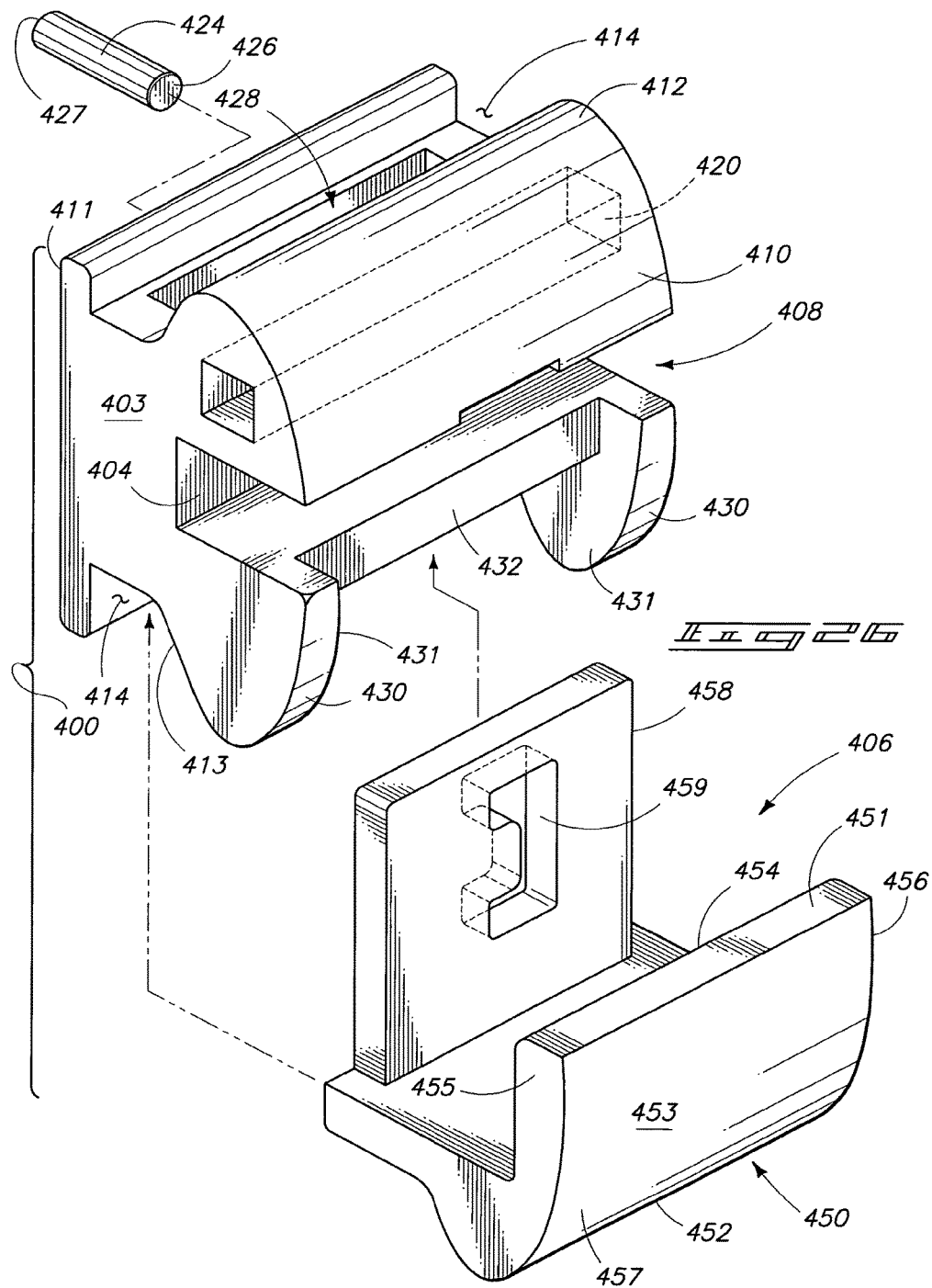

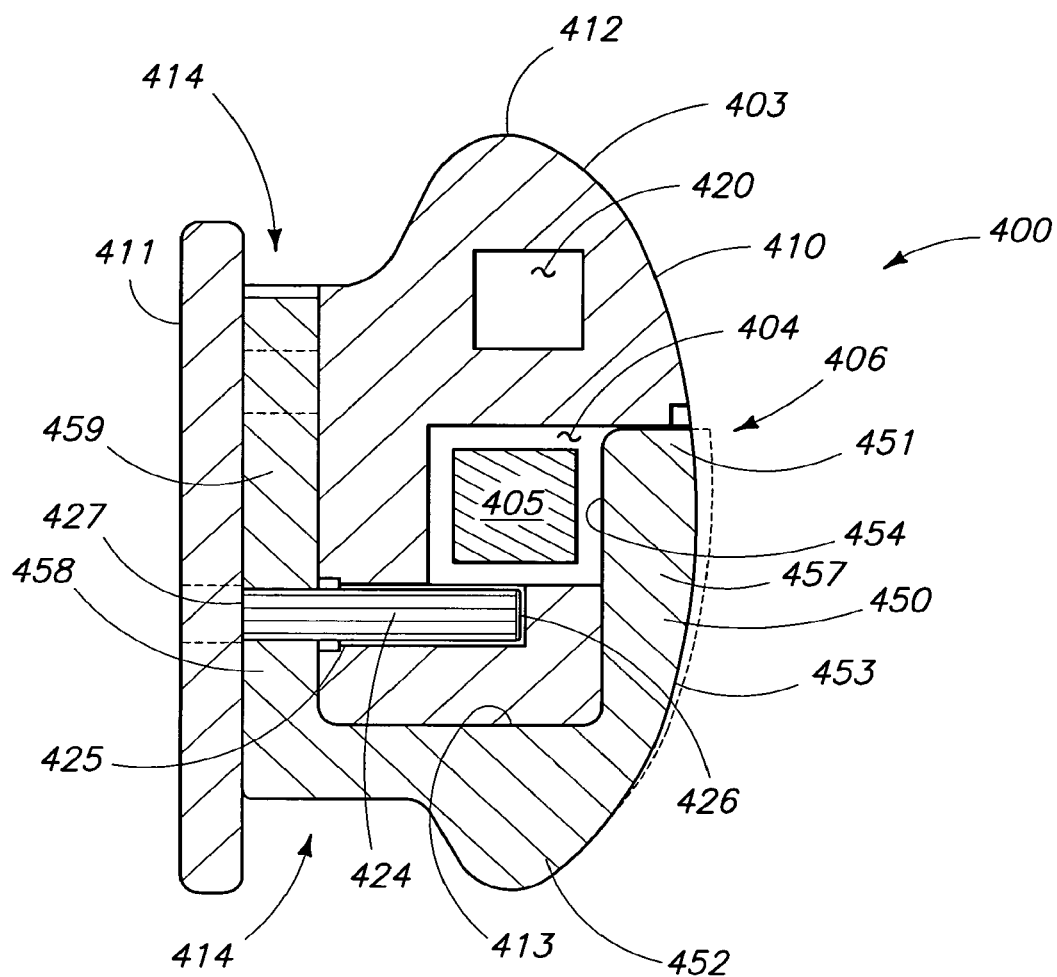

ORTHODONTIC BRACKET

CROSS-REFERENCE TO RELATED APPLICATION

This application is a continuation of U.S. patent application Ser. No. 14/971,012 filed Dec. 16, 2015, which is a continuation of U.S. patent application Ser. No. 12/755,054 filed Apr. 6, 2010, which is a divisional of U.S. patent application Ser. No. 11/408,873 filed Apr. 19, 2006 (U.S. Pat. No. 7,704,072), and is related to U.S. patent application Ser. No. 14/968,065 filed Dec. 14, 2015, and U.S. patent application Ser. No. 14/969,881 filed Dec. 15, 2015, the disclosures of which are incorporated by reference herein in their entirety.

TECHNICAL FIELD

This disclosure pertains to an orthodontic bracket, and more specifically to biased ligating slides which are employed with same.

BACKGROUND OF THE INVENTION

Orthodontic brackets which are attached to the teeth of a patient, are designed to engage an archwire that exerts force upon the teeth to move the teeth into various clinically appropriate orientations. Such brackets typically include an archwire slot for reception of the archwire. Those skilled in the art will recognize that an archwire slot can have any desired cross-sectional configuration, or size, to match the size and shape requirements of the archwire or wires that are being received within the same slot.

Heretofore, many orthodontic brackets have been adhesively bonded to a tooth with the archwire slot being oriented in a substantially parallel orientation relative to the occlusal plane. However, those skilled in the art have long recognized that the archwire slot can also be angularly oriented across the bracket for certain clinical applications. Previously, orthodontic brackets have included various cleat-like extensions which have been referred to in the art as tie-wings or lugs. These structures project upwardly and downwardly, typically in pairs, at the top and bottom of the installed orthodontic bracket. In this regard, these extensions permit an archwire to be held within the archwire slot of the bracket by means of a twisted wire (a ligature) or an elastomeric o-ring which is releasably affixed by the respective lugs or tie-wings.

In U.S. Pat. No. 4,248,588 to Hanson, and which issued on Feb. 3, 1981, an orthodontic bracket, and archwire were disclosed and which included a moveable retainer member which, in one position, could be located in a position which facilitated access to the archwire slot, and in a second position, was useful for retaining the archwire within the archwire slot. Still further, this same reference disclosed a passageway 74 which is defined, at least in part, by the body of the bracket, and which is useful, in one embodiment, to pass a thin tie wire through, but which also was found advantageous, when fabricated in a rectangular cross-section, to receive a secondary archwire which could be employed to provide additional corrective forces to the tooth upon which the orthodontic bracket was attached.

In my U.S. Pat. No. 5,466,151, I disclosed a spring-locked orthodontic bracket having a ligating slide and which was acted upon by a biasing spring of various configurations which exerted an anteriorly outwardly biasing force thereagainst the moveable ligating gate in order to position or secure it in an appropriate orientation relative to the archwire slot.

In my U.S. Pat. No. 6,071,118, I disclosed a self-ligating orthodontic bracket having a transverse archwire slot and which further included a moveable, ligating slide which cooperated with the orthodontic bracket in order to achieve various benefits not possible, heretofore, in orthodontic brackets having a similar design.

In addition to the foregoing, the Carriere SLB orthodontic bracket which has recently been introduced by Class One Orthodontics includes a bracket body with a moveable cantilevered ligating slide. This orthodontic bracket further includes resilient members which form an integral portion of the ligating slide and which cooperate with the superior portion of the bracket body to releasably secure the ligating slide in a closed position. In this arrangement, the members forming an integral portion of the ligating slide exert a force on the ligating slide which is substantially coaxially aligned relative to the path of travel of the ligating slide. The resilient members otherwise do not support the distal end of the ligating slide when it is located in closed position over the archwire slot. Thus, the ligating slide remains cantilevered relative to the archwire slot.

While the brackets of the prior art have worked with varying degrees of success, assorted shortcomings have detracted from their usefulness. In particular, one of the chief difficulties with brackets having the designs as discussed, above, relates to the accurate manufacturing of same. Still further, another shortcoming attendant with such prior art devices relates to the dimensional size of such brackets. As should be understood, practitioners, as well as patients, have continually sought after smaller, and more inconspicuous brackets in order to acquire or achieve a more aesthetically acceptable appearance when the bracket has been installed in the mouth of a patient. As will be clear from reviewing the several earlier mentioned prior art references, the positioning of a biasing member within the bracket body in order to biasingly cooperate with the ligating gate has typically increased the dimensional size of the resulting bracket, and further increased the difficulty associated with fabricating and assembling orthodontic brackets of this type. Additionally, orthodontic bracket designs such as the Carriere SLB have additional shortcomings. For example, in brackets of this prior art design, if an archwire is not fully seated in the archwire slot, it becomes difficult if not impossible to fully engage the ligating slide with the bracket body thereby securing the ligating slide in the closed position over the archwire. More specifically, in a design such as seen in the Carriere SLB, and wherein the cantilevered ligating slide must releasably engage the base member in order to remain closed over the archwire slot, it will be readily apparent that an unseated archwire may deflect or deform the ligating slide sufficiently so that it may not effectively engage the base member, and therefore remain closed over the archwire. In this specific design, if the ligating slide does not effectively engage the base member, a clinician may cause the ligating slide to complete disengage from the base member with the result that the base member must now be removed from the patients tooth, and a new orthodontic bracket attached to the tooth to continue treatment. This is obviously a time consuming process for both the clinician as well as the patient.

An orthodontic bracket which avoids many of the shortcomings attendant with the prior art practices and orthodontic bracket designs utilized heretofore, is the subject matter of the present application.

SUMMARY OF THE INVENTION

A first aspect of the present invention relates to an orthodontic bracket which includes a ligating slide coupled to a base member, and moveable along a path of travel relative thereto, and wherein a biasing member is borne by the ligating slide and cooperates with a portion of the base member to releasably position the ligating slide relative to the base member, and wherein the biasing member exerts a biasing force which acts in a direction which is substantially parallel to the path of travel.

Another aspect of the present invention relates to an orthodontic bracket which includes a base member defining an archwire slot having an opening, and at least one projection extending outwardly relative to the base member; a ligating slide moveably borne by the base member between a first position where the ligating slide is clear of the archwire slot, and a second position where the ligating slide projects over the opening of the archwire slot; and a biasing member borne by the ligating slide and slideably cooperating with the projection, and wherein the biasing member has a first portion which receives the projection when the ligating slide is in the first position, and a second portion which receives the projection when the ligating slide is in the second position.

Another aspect of the present invention relates to an orthodontic bracket which includes a base member defining a transverse archwire slot having an opening; a ligating slide borne by the base member and moveable along a path of travel relative to the archwire slot, and wherein the ligating slide is moveable between a first position where the ligating slide allows access to the archwire slot, and a second position, where the ligating slide projects over the opening, and restricts access to the archwire slot, and wherein a biasing member is mounted on the ligating slide and biasingly supports the ligating slide in at least one of the first or second positions, and wherein the biasing member exerts a biasing force in a direction relative to the base member which is substantially parallel and in non-coaxial alignment relative to the path of travel of the ligating slide.

Still further, another aspect of the present invention relates to an orthodontic bracket which includes a base member having a transverse archwire slot defining an opening, and at least one projection extending outwardly from the base member; a ligating slide moveable between a first position which is clear of the archwire slot, and a second position where the ligating slide projects over the opening of the archwire slot; and a substantially planar biasing member borne by the ligating slide and matingly cooperating with the projection, and wherein a first portion of the biasing member receives the projection when the ligating slide is in the first position, and a second portion of the biasing member receives the projection when the ligating slide is in the second position.

Another aspect of the present invention relates to an orthodontic bracket which includes a base member having a posterior facing surface, an anterior facing surface, and a projection extending outwardly from one of the posterior and/or anterior facing surfaces; and a ligating slide moveably borne by the base member along a path of travel, and further having a pair of members having opposing surfaces, and a channel defined therebetween the opposing surfaces, and wherein the pair of members resiliently cooperate with the projection to exert a biasing force on the ligating slide which is in substantially parallel spaced relation relative to the path of travel.

Yet another aspect of the present invention relates to an orthodontic bracket which includes a base member having a posterior facing surface, and an anterior facing surface, and wherein a projection extends outwardly from the posterior facing surface, and wherein the anterior facing surface of the base member defines, at least in part, an archwire slot having an opening; and a ligating slide is borne by the base member and is moveable between a first position, which allows access to the archwire slot through the opening, and a second position, which restricts access to the archwire slot through the opening, and wherein the ligating slide comprises a first portion extending to a second portion, and wherein the first portion forms, at least in part, a portion of the anterior facing surface of the base member, and the second portion is positioned in adjacent spaced relation relative to the posterior facing surface of the base member; and a resilient-biasing member is made integral with the second portion of the ligating slide and which resiliently cooperates with the projection.

Still further, another aspect of the present invention relates to an orthodontic bracket which includes a base member; an archwire slot traversing the base member, and wherein the archwire slot defines an opening within an anterior surface of the base member; a channel extending along the anterior surface of the base member from the archwire slot to a lowermost surface of the base member; a fixed projection extending laterally outwardly from the base member, and into a portion of the channel; a ligating slide which is slideably received in the channel; and a biasing member borne by the ligating slide and which resiliently cooperates with the fixed projection.

Still another aspect of the present invention relates to an orthodontic bracket which includes a ligating slide having a biasing member which is defined, in part, by a pair of members with opposing surfaces, and wherein the opposing surfaces define a channel therebetween, and wherein the members are spaced and resiliently moveable one relative to the other; and are operable to exert a biasing force on the ligating slide, and wherein the ligating slide is moveable along a path of travel, and the biasing force is substantially parallel and in spaced relation relative to the path of travel; and a biasing abutment is defined by one of the surfaces of one of the members, and wherein the biasing abutment at least partially occludes the channel.

Another aspect of the present invention relates to an orthodontic bracket which includes a base member having anterior and posterior facing surfaces, and further defining an archwire slot having an opening in the anterior facing surface; a ligating slide moveably borne by the base member, and which is moveable between a first position which is clear of the archwire slot, and a second position where the ligating slide projects over the archwire slot; and a biasing member borne by the base member and resiliently cooperating with the ligating slide, and wherein the biasing member exerts a biasing force which is directed posteriorly outwardly relative to the base member to position the ligating slide in the first and second positions.

Another aspect of the present invention relates to an orthodontic bracket which includes a base member defining an archwire slot; a ligating slide borne by the base member and moveable between a first, open position which allows access to the archwire slot, and a second, closed position which restricts access to the archwire slot, and wherein the ligating slide has an anterior and a posterior facing surface, and wherein a channel is formed in the posterior facing surface of the ligating slide; and an elongated flexible member is borne by the base member and which has a distal end which is received in the channel, and wherein the distal end is resiliently deformable along a substantially arcuately shaped path of travel, and wherein the flexible member cooperates with the channel to releasably secure the ligating slide in the first and second positions.

Yet still another aspect of the present invention relates to an orthodontic bracket which includes a base member defining an archwire slot; an elongated flexible member borne by the base member and which has a distal end which is moveable along an arcuately shaped path of travel; and a ligating slide moveably borne by the base member between a first position where the ligating slide is clear of the archwire slot, and a second position where the ligating slide restricts access to the archwire slot, and wherein the distal end of the elongated flexible member cooperates with the ligating slide and moves along the arcuately shaped path of travel as the ligating slide moves between the first and second positions.

A further aspect of the present invention relates to an orthodontic bracket which includes a base member having an anterior and posterior facing surfaces, and which further defines a transverse archwire slot having an opening; a ligating slide which is moveably borne by the base member between a first position, where the ligating slide is clear of the archwire slot, and a second position, where the ligating slide projects over the opening of the archwire slot, and wherein the ligating slide moves along a path of travel between the first and second positions; a resilient member borne by the base member and cooperating with the ligating slide to releasably restrain the ligating slide in the first and second positions, and wherein the resilient member is resiliently deformed, and moves along an arcuately shaped path of travel when the ligating slide moves between the first and second positions; a transverse passageway formed in the base member and disposed in spaced relation relative to the archwire slot; and an orthodontic appliance received, at least in part, in the transverse passageway and which facilitates passive self-ligation.

Yet still another aspect of the present invention relates to an orthodontic bracket which includes a base member defining an archwire slot, and which has anterior, posterior, superior and inferior facing surfaces, and where the base member defines a passageway which is located adjacent to the posterior facing surface and which extends therebetween the superior and inferior facing surfaces; an elongated flexible member borne by the base member and extending posteriorly outwardly relative to the base member and into the passageway, and wherein the elongated flexible member has a distal end which is moveable along an arcuately shaped path of travel; and a ligating slide which is received, at least in part, in the passageway, and which cooperates with the elongated flexible member, and wherein the ligating slide is moveable from a first position where the ligating slide is clear of the archwire slot, to a second position where the ligating slide restricts access to the archwire slot.

BRIEF DESCRIPTION OF THE DRAWINGS

Preferred embodiments of the invention are described below with reference to the following accompanying drawings.

FIG. 5 is a greatly enlarged, front elevation view of one form of an orthodontic bracket of the present invention, and which shows the ligating slide positioned so as to allow access to the archwire slot.

FIG. 6 is a fragmentary, front elevation view of a ligating slide which is useful in one form of the orthodontic bracket of the present invention.

FIG. 7 is a transverse, substantially horizontal, sectional view taken from a position along the line 7-7 of FIG. 6.

FIG. 8 is a transverse, vertical, sectional view taken from a position along the line 8-8 of FIG. 6.

FIG. 9 is a fragmentary, side-elevation view of a substantially planar biasing member which finds usefulness in one form of the orthodontic bracket of the present invention.

FIG. 10 is a perspective, exploded, front elevation view of the first form of the orthodontic bracket of the present invention, and with some underlying surfaces shown in phantom lines.

FIG. 11 is a front elevation view of a second form of an orthodontic bracket of the present invention.

FIG. 13 is a front elevation view of a second form of an orthodontic bracket of the present invention, and which shows a ligating slide associated with same and which is located in a first position which permits access to the archwire slot and which is defined by the orthodontic bracket.

FIG. 14 is a front elevation view of the ligating slide employed with the second form of the orthodontic bracket of the present invention.

FIG. 15 is a transverse, vertical, sectional view taken from a position along the line 15-15 of FIG. 14.

FIG. 16 is a fragmentary, rear elevation view taken from a position along line 16-16 of FIG. 12.

FIG. 17 is a perspective, exploded, front elevation view of the second form of the orthodontic bracket of the present invention.

FIG. 17A is a perspective, exploded, front elevation view of yet another form of the orthodontic bracket of the present invention.

FIG. 18 is a transverse, vertical sectional view of a third form of the orthodontic bracket of the present invention.

FIG. 24 is a fragmentary, front elevation view of a ligating slide which is useful in the fourth form of the orthodontic bracket of the present invention.

FIG. 25 is a transverse, substantially horizontal, sectional view taken from a position along line 25-25 of FIG. 24.

FIG. 26 is a perspective, exploded, front elevation view of a fifth form of the orthodontic bracket of the present invention.

FIG. 27 is a transverse, vertical sectional view of the fifth form of the orthodontic bracket as seen in FIG. 26.

DETAILED DESCRIPTION OF THE PREFERRED EMBODIMENTS

Figure 1:
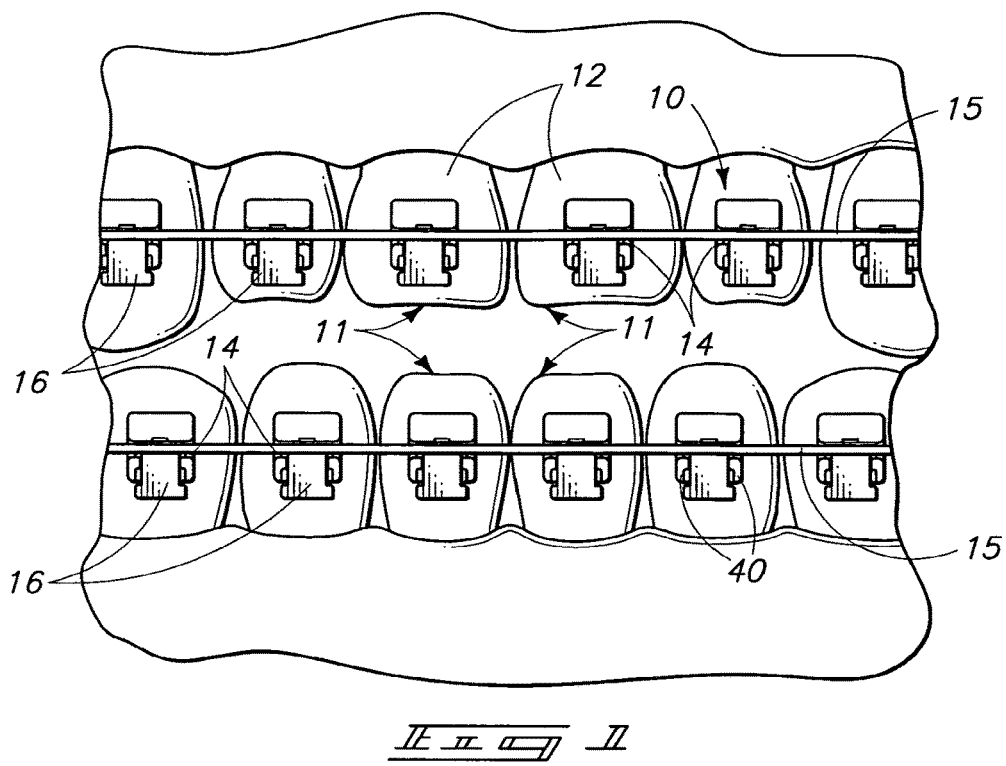
FIG. 1 is a partial, greatly enlarged view of one form of the orthodontic bracket of the present invention, and where the invention is illustrated within a patient's mouth and having an archwire received in same, and further where the ligating slide is positioned so as to permit access to the archwire slot.
Figure 2:
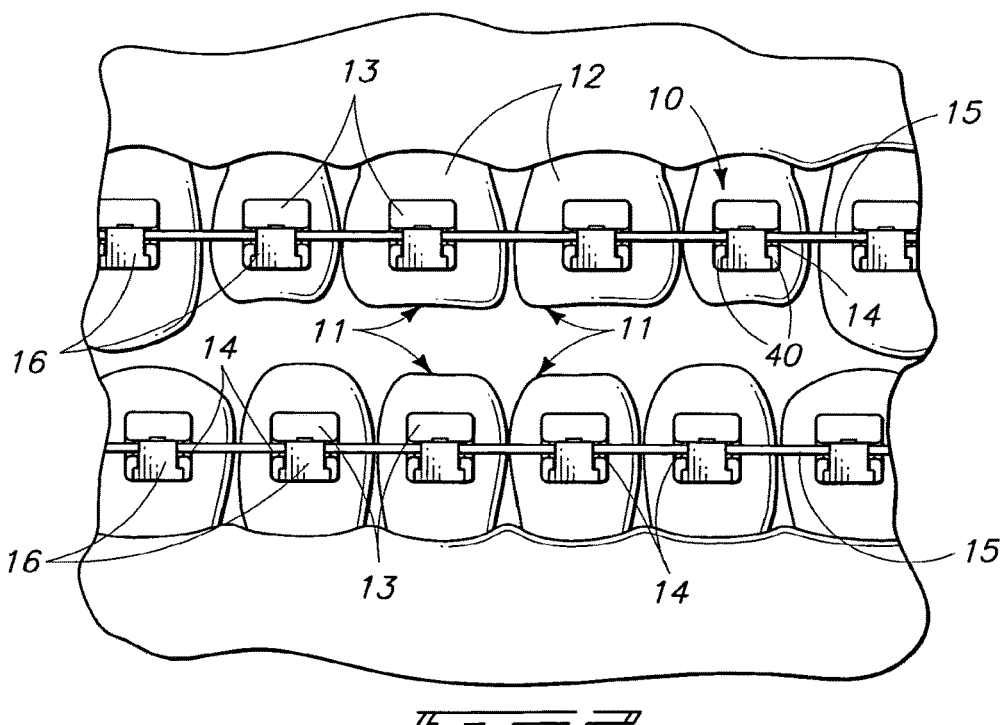
FIG. 2 is a partial, greatly enlarged view of one form of an orthodontic bracket of the present invention, and which shows the ligating slide associated with same in a position which restricts access to the archwire slot defined by the orthodontic bracket.

This disclosure of the invention is submitted in furtherance of the constitutional purposes of the U.S. Patent Laws "to promote the progress of science and useful arts" (Article 1, Section 8).

First Embodiment

Five forms of a self-ligating orthodontic bracket are illustrated in the drawings. A first embodiment is shown in FIG. 1-10; a second form is illustrated in FIGS. 11-17; a third form is shown at FIG. 18; a fourth form is shown in FIGS. 21-25; and a fifth form is shown in FIGS. 26 and 27, respectively. Other inventive aspects of the present invention such as a novel orthodontic appliance to be employed in the various forms of invention (FIG. 19) are also shown in the various views, and will be discussed in greater detail in the paragraphs hereinafter.

The illustrated details of the orthodontic bracket of the present invention may be used in many different combinations within the scope of this disclosure. For this reason, the details of the illustrated orthodontic brackets, as described hereinafter, are intended to be interpreted as merely illustrative, and should not be taken as restrictive of the practical combinations of such features within the scope of this disclosure and the appended claims as provided for, hereinafter. When referring to the illustrated forms of the bracket assemblies, and their component parts, the front surfaces, that is, directed outwardly from a supporting tooth shall be referred to as the anterior surface. Conversely, its rear surfaces, that is, those facing toward the tooth shall be termed the posterior surfaces. Directions along a bracket assembly generally parallel to the incisal or occlusal line or plane shall be referred to as having width and/or being transverse. Conversely, perpendicular directions extending in generally upright orientations between the gingival line, and the incisal, or occlusal line shall be referred to as the height of the bracket assembly. The upright surfaces across the bracket shall be termed its side surfaces, and surfaces along the top and bottom of the bracket assembly shall be termed the incisal or occlusal surfaces or the gingival surfaces, respectively. When referring to the directions of movement of the ligating slide of the present orthodontic bracket the terms inferior and superior shall be used in an anatomical sense, that is, oriented in relation to a patient wearing the bracket. Thus, if a ligating slide is moved inferiorly, it will be moved in a downward direction. Conversely, if it is moved superiorly, it will be moved in an upward direction.

The archwire slot shown in the attached drawings are aligned transversely across each bracket in a direction which is usually parallel to the incisal or occlusal surfaces for general illustration purposes, only. However, the archwire slot across each bracket can be oriented in any desired angular configuration relative to its incisal or occlusal surfaces to affect a desired degree of tipping to a supporting tooth. In addition, the bracket can be oriented angularly relative to a supporting pad thereby providing an angular force to the archwire slot, and engaged archwire, when secured to a supporting tooth.

In order to properly fit upon the exterior surface of a selected tooth, the posterior surface, across the pad for each bracket, must be molded or otherwise formed to conform to the tooth with the archwire slot at the desired angular relationship to the archwire upon installation. Various placement angles can be provided on selected brackets by rotating the anterior surface contour across the pads of the brackets within a set. Alternatively, the archwire slots, and a set of brackets can be arranged in selected angles by rotating the position of the protruding elements of each bracket relative to a pad having a properly contoured posterior surface. The archwire slot is then formed in the protruding portion of the bracket to match the amount of tipping to be imparted to a given tooth. While the illustrated archwire slot in the various forms of the invention is shown in a perpendicular orientation relative to the anterior surface of the bracket, it could be formed in any desired angle relative to the anterior surfaces, depending upon the desired torquing to which the supporting tooth is to be subjected. The illustrative brackets, as shown herein, are designed to be bonded directly to a tooth at either the facial or lingual tooth surfaces.

The present bracket can be made from any suitable material including metals, plastics and ceramics, as well as a combination of such materials. The brackets, as shown herein, are typically fabricated out of metal, but the choice of materials is not critical to the understanding or the subsequent clinical use of the invention. The only limitation with regard to the chosen materials is the ability to efficiently fabricate or mold the bracket, and the accompanying ligating slide as structures which are capable of movement one relative to the other, and which are operable to engage the archwire during an orthodontic procedure.

Figure 3I:
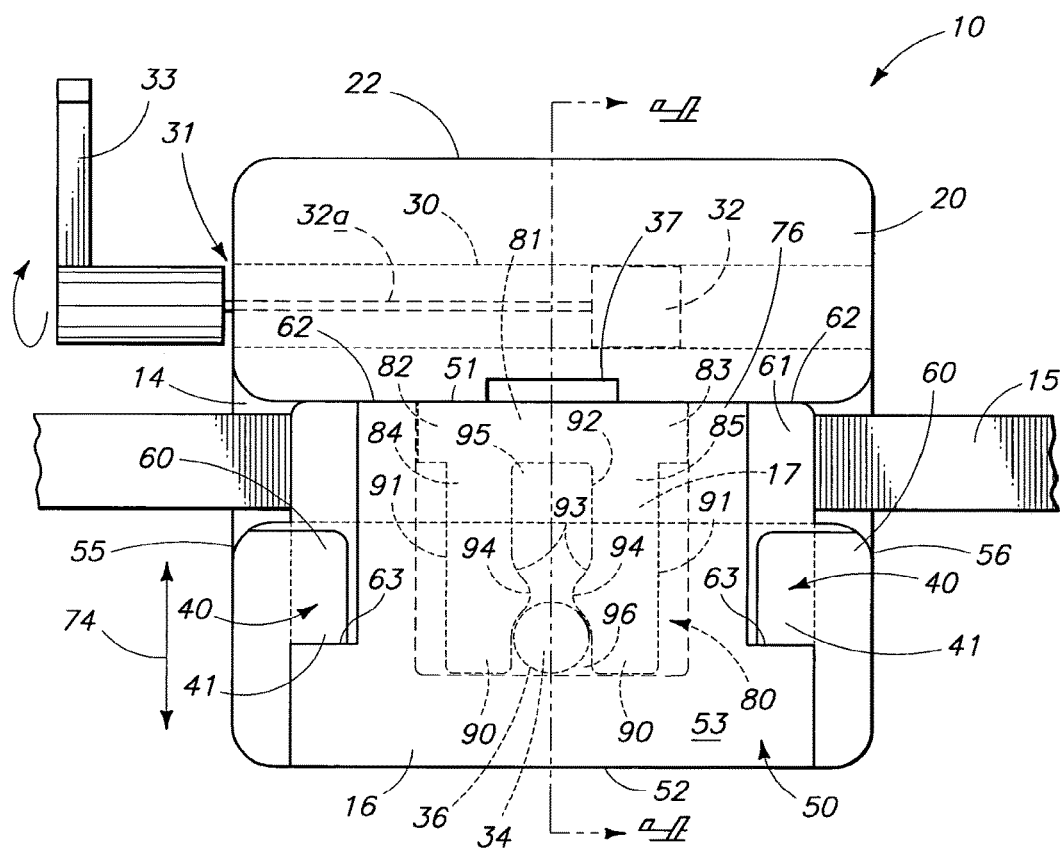
FIG. 3 is a greatly enlarged front elevation view of a first form of an orthodontic bracket of the present invention.
FIG. 3A is a greatly enlarged front elevation view of a first form of an orthodontic bracket of the present invention, and which is utilized in combination with another orthodontic appliance.

Referring now to FIGS. 1-10, a first form of an orthodontic bracket of the present invention is generally indicated by the numeral 10 therein. As seen more specifically in FIG. 1, the orthodontic bracket 10 finds usefulness when used in an orthodontic procedure which affects a plurality of teeth 11 within a patient's mouth. As well known to those skilled in the art, each of the teeth 11 have an exterior facing surface 12 upon which a bracket body or base member 13 is typically affixed by using an appropriate adhesive. With reference to FIGS. 1 and 3, it will be seen that the base member or bracket body 13 defines a substantially transversely disposed archwire slot 14 which extends thereacross, and which is further operable to receive a suitable archwire 15 therein. The archwire is illustrated in an appropriate, seated position within the archwire slot. It will be recognized, however, under some circumstances and particularly when the archwire is first installed, it may not be appropriately positioned within the archwire slot. The present invention, as will be described below, is operable to facilitate passive self-ligation of the archwire in a fashion not possible, heretofore. For example, during the treatment of a patient, orthodontic brackets occasionally detach from the underlying tooth. Further, teeth occasionally move following this detachment. If his occurs, the various forms of the orthodontic bracket as will be disclosed, herein, can be reattached to the tooth at its correct position, and the archwire 15 may be reinserted into the archwire slot 14, and the ligating slide closed, without the need to replacing the archwire 15 with a smaller dimensioned archwire which is now the accepted practice. This feature of the invention is facilitated by the resiliency of the ligating slide 16 which will be described in greater detail, hereinafter. Additionally, the present invention provides significant time savings for the treatment of a patient. In the first form of the invention, the base member further cooperates with a moveable ligating slide or gate 16, which in one position as seen in FIG. 5, allows access to the archwire slot 14; and in FIG. 3 restricts access to the archwire slot 14. The ligating slide cooperates with a substantially planar, resilient biasing member 17 as seen in FIGS. 3 and 9, and which defines, at least in part, the course of movement for the ligating slide 16. Therefore, in its broadest aspect, the present invention relates to an orthodontic bracket 10 which includes a ligating slide 16 which is configured to be coupled to a base 13, and wherein the ligating slide 16 further cooperates with a biasing member 17 which receives a portion of the base member 13.

Figure 4:
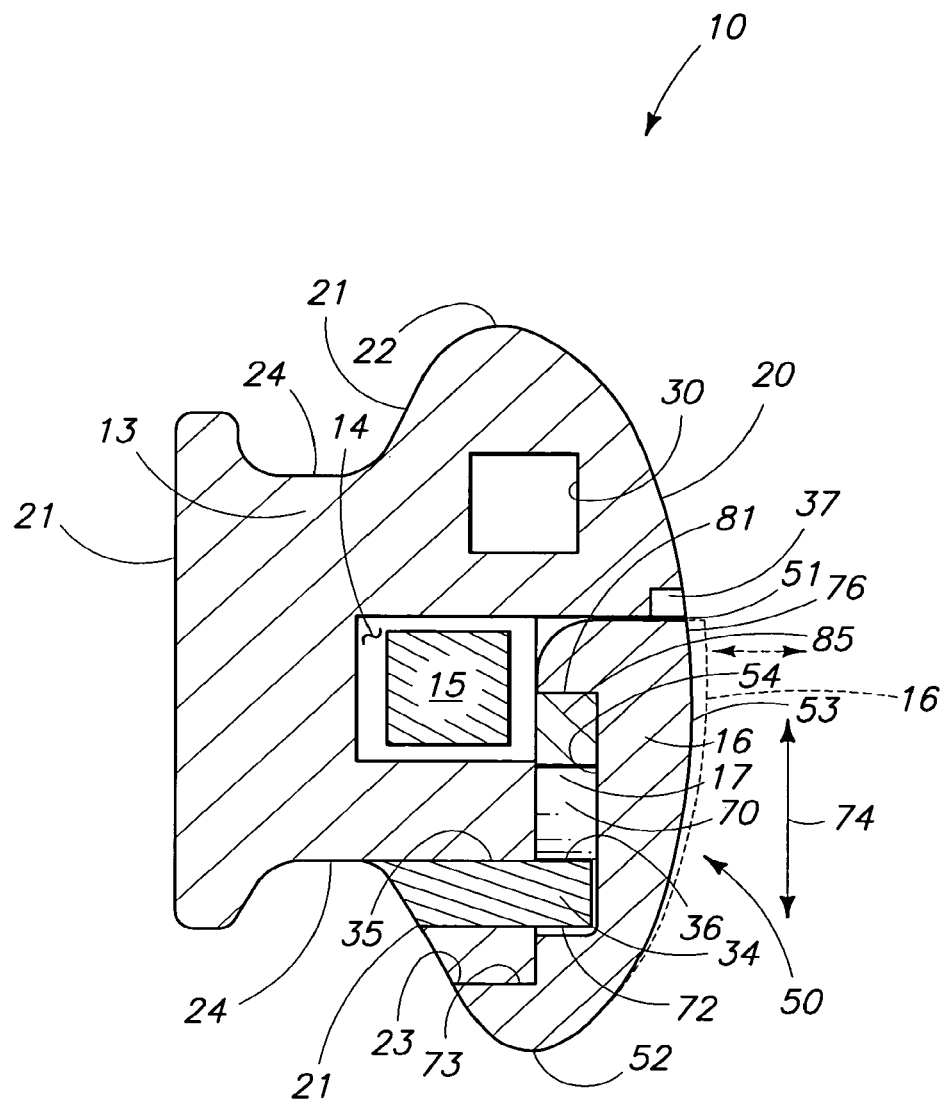
FIG. 4 is a transverse, vertical, sectional view of one form of the orthodontic bracket of the present invention, and which is taken from a position along the line 4-4 of FIG. 3.

Referring now to FIG. 4, it will be seen that the bracket body or base member 13 has an anterior facing surface or side 20, and an opposite posterior facing surface or side 21 which is adhesively affixed to the exterior surface 12 of a tooth 11 of a patient. The base member 13 further has a top, or superior facing surface or portion 22, and an opposite, lower, or inferior surface or portion 23. As seen in FIG. 4, opposite transversely oriented channels 24 are defined in the superior and inferior facing surfaces and are further located therebetween the anterior and posterior facing surfaces 20 and 21. These channels may be useful for securing various other dental appliances therein. More specifically, the superior portion 22 and inferior or lowermost portion 23 define substantially continuous upper and lower tie wing projections which can be employed in various orthodontic treatment regimens.

Figure 12:
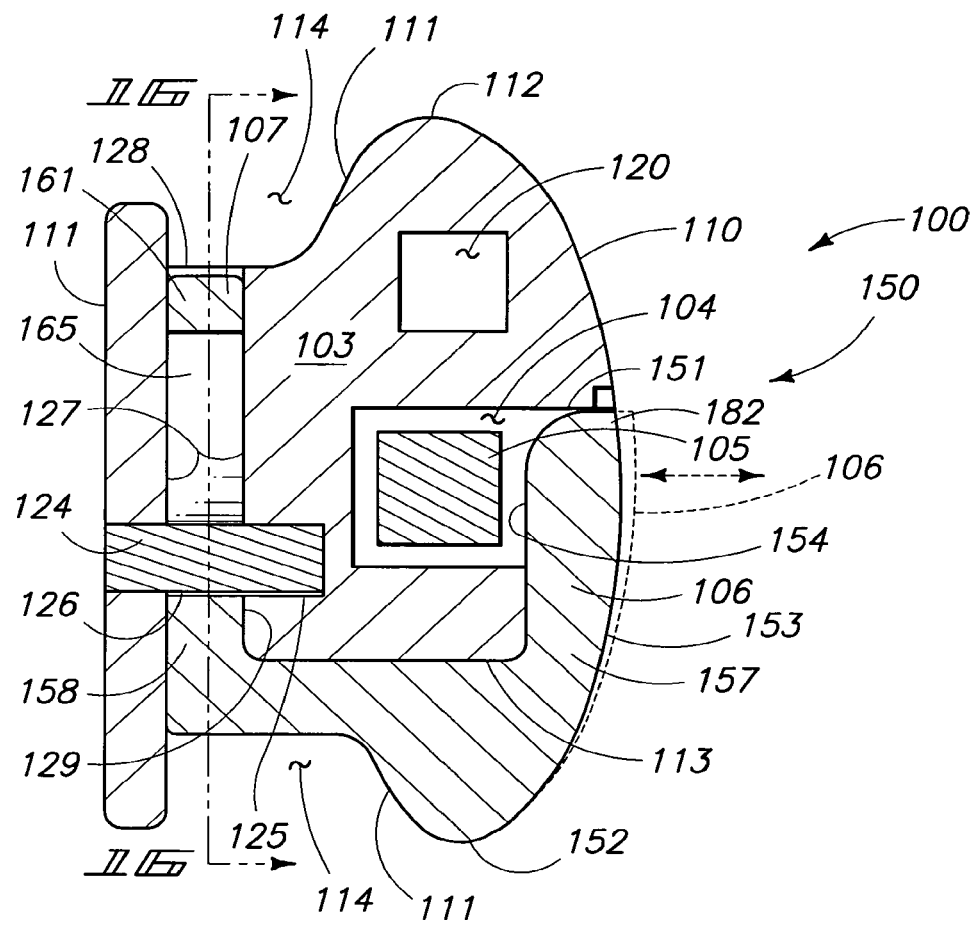
FIG. 12 is a transverse, vertical, sectional view taken from a position along the line 12-12 of FIG. 11.

Referring still to FIG. 4 and FIG. 10 it will be seen that the bracket body or base member 13 has a transverse, substantially square or rectangular shaped passageway 30 formed in the superior portion 22 of the base member. As illustrated in FIG. 10, it will be seen that the transverse passageway extends completely through the base member, and further is disposed in substantially parallel, spaced relation relative to the archwire slot 14. As should be understood, if the archwire slot 14 is located in an orientation other than the transverse orientation as seen in FIGS. 1-10, then this parallel orientation would not exist. However, it should be understood that the transverse passageway 30 may receive or cooperate with another secondary archwire; post; and/or other orthodontic appliances as will be described, hereinafter, and which may be useful in treating various tooth anomalies. In this regard, and referring now to FIGS. 3, 5 and 19, a novel orthodontic appliance in the form of a torquing assembly 31 is provided, and which matingly cooperates with the transverse passageway 30 in a manner so as to supply force of various amounts, and directions to the underlying tooth 11. In this regard, the torquing assembly 31 has a first portion 32 having a substantially square or rectangular shape, and which is dimensioned to be telescopingly received within the transverse passageway 30. Still further, the torquing assembly 31 has a second portion 33 which is attached to the first portion 32, by means of an intermediate portion 32A. The intermediate portion is longitudinally, resiliently deformable by means of the second portion 33, and which may be rotated thereabout the first portion 32, and then left in engagement with the archwire 15 as seen in FIG. 5. In this fashion, the torquing assembly 31 can produce a force of a given magnitude, and direction, on the tooth of a patient in order to further enhance the usefulness of the present orthodontic bracket 10. As seen further in FIG. 4, and in the other views, the present orthodontic bracket 10 includes at least one post or projection 34 which extends outwardly relative to the base member 13, and which further is received within a bore 35 which is formed in the base member 13 and near the inferior portion or surface 23. In the present invention, the post or projection 34 is received, at least in part, in the bore 35, and extends anteriorly outwardly relative to the base member 13. Further, and as will be discussed in the second form of the invention as seen in FIG. 12, the post or projection 124 extends posteriorly outwardly relative to the base member 103. As should be understood, the projection 34 is herein depicted as being substantially cylindrical (FIG. 10), and further the projection 34 has an exterior facing surface 36. As will be discussed in greater detail hereinafter, the projection 34 cooperates with the ligating slide 16 in order to define, at least in part, a course of movement for the ligating slide. This feature of the invention will be discussed, below. As earlier noted, the base member 13 has an anterior facing surface or side 20; and a posterior facing surface or side 21. In the first and second forms of the invention as described herein, the bore 35 is sized so as to matingly receive and secure the projection 34. In the assembly of the present invention, it should be understood that the projection 34/124 will be inserted in the bore 35/125 from the posterior facing surface or side 21 of the base member 13/103, respectively. As will be recognized from a study of the drawings, in some forms of the invention, the bore 35 may extend through the base member 13 (FIG. 4); but in a second form of the invention, the bore 125 may not extend through the base member 103.

As seen in FIGS. 3 and 4, a recess 37 is formed in the anterior facing surface 20 and adjacent the archwire slot 14. This recess is useful for inserting a dental tool or other instrument therein in order to affect downward or inferior movement of the ligating slide 16 as will be discussed in greater detail hereinafter.

Figure 4A:
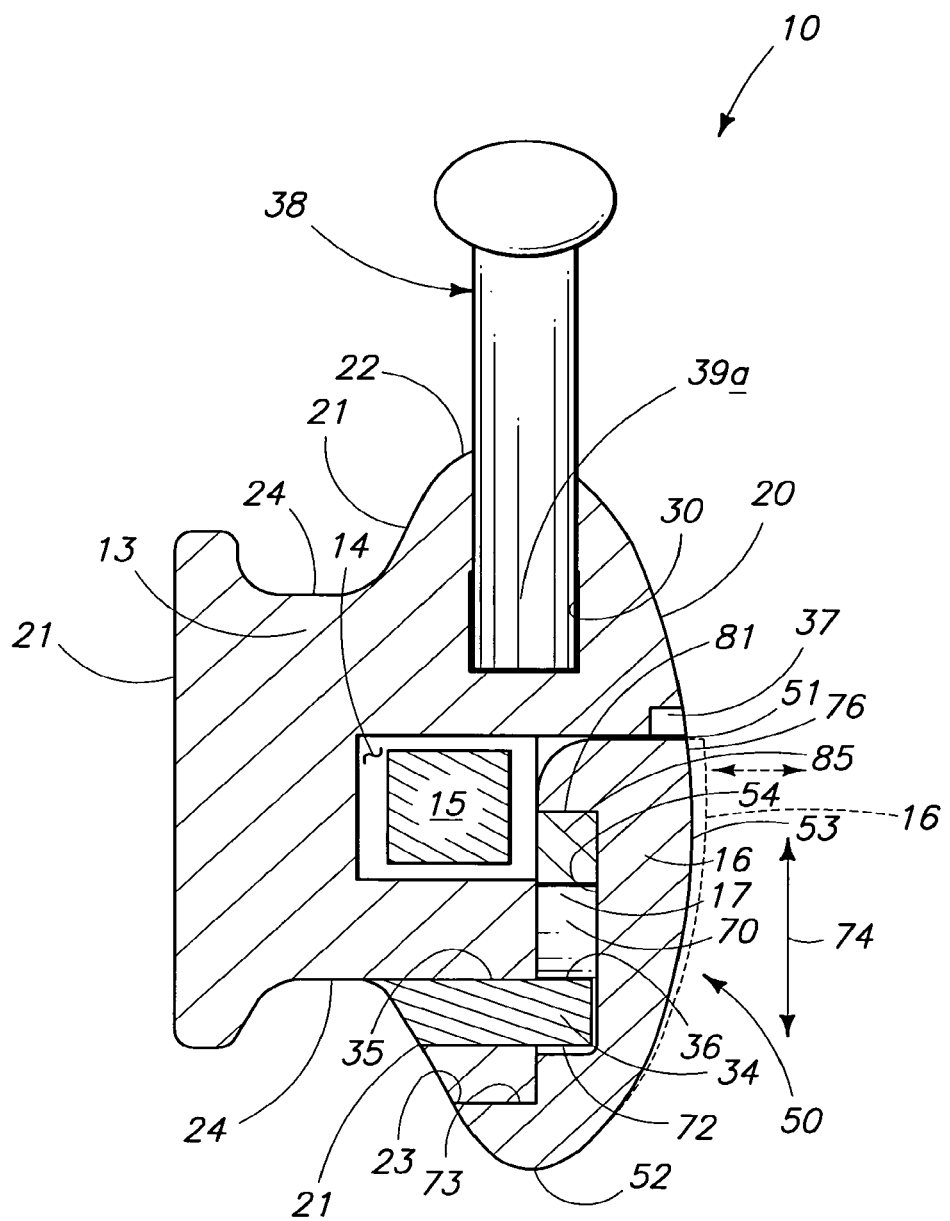
FIG. 4A is a transverse, vertical, sectional view of one form of the orthodontic bracket of the present invention, and which is taken from a position along the line 4A-4A of FIG. 3A.

As best seen in FIGS. 3A and 4A, the present invention can accommodate a second novel orthodontic appliance in the form of a removable horizontal hook 38, and which can be inserted into the passageway 30, and which can cooperate with elastic bands or other appliances of various sorts in order to be employed in desired orthodontic treatment regimens. The removable horizontal hook has a rectangular shaped main body 39 which is dimensioned for mating receipt with the passageway 30. The main body has a distal end 39A which may be bent or otherwise deformed, as illustrated by phantom lines, in order to secure the removable hook within the passageway 30.

As seen in FIG. 10, the anterior facing surface 20 of the base member 13 defines a pair of spaced, substantially inwardly extending, guide members which are generally indicated by the numeral 40. The guide members 40 have an exterior facing surface 41, and an opposite, interior facing surface 42 which defines, at least in part, a generally vertically oriented ligating slide channel which is generally indicated by the numeral 43. As illustrated in FIG. 10, the projection 34 extends anteriorly outwardly from the base member 13, and into this ligating slide channel 43 for purposes of cooperating with the ligating slide 16 which will be described below. As seen in FIG. 10, the bracket body or base member 13 defines an opening 44 which allows access to the archwire slot 14 when the ligating gate is in one of its two operational positions. As seen in the drawings, the archwire slot 14 communicates with the channel 43. The operation of the ligating slide or gate 16 will be described in greater detail in the paragraphs which follow.

Referring now to FIGS. 3-7, it will be seen that the first form of the orthodontic bracket 10 includes a ligating slide 16 which is slideably borne by the base member 13 and reciprocally moveable along a path of travel relative to the archwire slot 14 in the fashion which will be described, hereinafter. The ligating slide has a main body 50 having a first, superior end 51; a second inferior end 52; an anterior facing surface 53; and an opposite, posterior facing surface 54. As seen, most clearly in FIGS. 4 and 10, the superior end 51 may be beveled or otherwise rounded so as to facilitate passive self-ligation of the archwire 15. Still further, the main body includes a first, vertically disposed peripheral edge 55; and a second, opposite vertically disposed peripheral edge 56 which is disposed in substantially parallel, spaced relation relative to the first peripheral edge 55. As will be seen by reference to FIG. 10, for example, the guide members 40, and the lowermost portion 23 of the base member 13 shields, at least in part, a portion of each of the opposite peripheral edges 55 and 56, respectively. As further seen by reference to FIG. 4, for example, the ligating slide 16 is resiliently deformable, as seen by the phantom lines of the ligating slide, to a position which is anteriorly outward relative to the base member 13. This resiliently deformable ligating slide 16 facilitates passive self-ligation of the archwire inasmuch as the archwire 15 need not be fully seated in the archwire slot 14, for the orthodontic bracket 10 to be effectively used. The beveled and/or rounded superior end allows the ligating slide to move past the bracket body or base member 13 when moving from a displaced, biased position, as seen in phantom lines in the drawings to an unbiased orientation.

Referring now to FIGS. 3-8 and 10, it will be seen that a first recessed region 60, and a second recessed region 61 are formed in the anterior facing surface 53 of the ligating slide 16, and adjacent to the first and second vertically disposed edges 55 and 56, respectively. These first and second recessed regions 60 and 61, respectively, each have a first end 62, which is positioned adjacent to the first, superior end 51 of the main body; and a second end 63, which is spaced therefrom, and oriented in spaced relation relative to the second inferior edge 52. As seen in the drawings, the first and second recessed regions have a thickness dimension which facilitates the positioning of the recessed regions in the area therebetween the interior facing surface 42 of the respective guide members 40, and the base member 13 so as to permit the selective slideable movement of the ligating slide 16 in the channel 43. As should be understood, this physical arrangement prohibits force which might be occasioned by a patients chewing, for example, from adversely influencing the ligating slide 16. As will be appreciated from a study of FIGS. 7 and 8, a cavity 70, of predetermined dimensions, is formed in the posterior facing surface 54 of the main body 50, and is operable to receive the planar resilient biasing member 17 which will be discussed in greater detail, below. The cavity 70 has an open, first or superior end 71 (FIG. 8), and an opposite, closed, second or inferior end 72. The cavity has a depth dimension which is greater than or equal to the thickness dimension of the substantially planar, resilient biasing member 17. Still further, the posterior facing surface 54 defines an abutting edge 73 which is operable to limit the movement of the ligating slide 16 along the course or path of travel 74 (FIG. 3). In this regard, the course of travel 74 is defined between a first position 75 where the ligating slide allows access to the archwire slot (this is best seen in FIG. 5); and a second position 76 where the ligating slide 16 projects in a cantilevered fashion, at least in part, over the opening 44 and, at least partially restricts access to the archwire slot 14 (FIG. 3). As earlier discussed, in other possible forms of the invention, the superior end 51 of the ligating slide may partially overlap and even releasably cooperate with the base member 13 to achieve the benefits provided by the present invention. In the arrangement as seen in the drawings, and as will be discussed below, the ligating slide 16 is biasingly supported in at least one of the first or second positions 75 and 76 respectively. As will become more apparent from the discussion which follows, the biasing force applied to the ligating slide 16 to support it in one of the first or second positions 75 and 76, acts in a direction which is substantially parallel to the path of travel 74 of the ligating slide 16. This is contrary to the prior art devices used heretofore, and wherein prior art biasing assemblies typically provided a biasing force which was directed anteriorly outwardly and in a direction which is generally normal to the ligating slide. As will be appreciated by a study of FIG. 4, the first superior end, or edge 51 may be disposed in juxtaposed abutting relation relative to the base member 13 when the ligating slide 16 is in the second position 76. In other possible forms of the invention, the same superior end or edge 51 may partially abut the base member 13; or as discussed above, partially overlay the base member 13. In still other arrangements, the superior end or edge 51 may releasably engage or otherwise cooperate with the base member when disposed in the second position where the ligating slide 16 extends over the archwire slot 14. In still other forms of the invention as seen in the drawings, the superior end 51 may be beveled and/or rounded so as to facilitate passive self-ligation. This feature is common to the several exemplary forms of the invention as seen in the drawings.

Referring now to FIGS. 3-10, it will be seen that the orthodontic bracket 10 of the present invention includes a substantially planar resilient biasing member 17 which is borne by the ligating slide 16, and which slideably cooperates with the projection 34 to biasingly support the ligating slide 16 in at least one of the first or second positions 75 and 76, respectively. In this regard, the resilient member 80 has a substantially planar main body 80 which is positioned in a generally parallel, spaced relationship relative to the anterior facing surface 53 of the ligating slide 16. As seen in the drawings, the substantially planar main body 80 is received within the cavity 70 which is defined by the ligating slide, and is oriented in a fashion so as to resiliently cooperate with the projection 34 which extends anteriorly outwardly relative to the base member 13. As illustrated, it will be appreciated that the resilient biasing member provides a resilient or biasing force which acts in a perpendicular or radial direction relative to the projection 34, and substantially parallel relative to the path of movement of the ligating slide 16. In this regard, and as seen in FIG. 9, the planar main body includes a transverse portion 81 which has a first end 82, and an opposite second end 83. The transverse portion 81 has a length dimension which is less than about the width dimension of the cavity 70 thereby allowing the main body 80 to be securely received within the cavity 70. Still further, the main body 80 includes first and second dependent, and resiliently moveable members 84 and 85, respectively. The respective depending members extend substantially normally, downwardly relative to the transverse portion 81. Still further, each of the depending members has a distal end 90; an outwardly facing edge 91; and an inwardly facing edge 92. The inwardly facing edges are disposed in predetermined, spaced relation one relative to the other. As seen in FIG. 9, a channel 93 is defined therebetween the inwardly facing edges 92. Still further, a portion of the inwardly facing edges 92, each define, at least in part, an inwardly facing biasing abutment 94 which mechanically and slideably cooperates or otherwise engages the projection 34 in order to bias the ligating slide 16 in one of the first or second positions 75 and 76, respectively. As understood from the drawings, the transverse portion 81 cooperates with the projection 34 to limit downward movement of the ligating slide 16, and to prevent the ligating slide from disengaging from the base portion 13 when the ligating slide is in the first position 75. As currently arranged, the respective biasing abutments 94 are operable to bias or otherwise releasably support the ligating slide 16 into the second position 76, which as seen in FIG. 3, substantially restricts access to the archwire slot 14 and thereby captures the archwire 15 therein. As seen in FIG. 9, the channel 93 has a first portion 95; and a second portion 96. The first and second portions of the channel 93 are located on the opposite sides of the respective biasing abutments 94. As seen, the respective biasing abutments are disposed in such an orientation so as to occlude, at least in part, or otherwise narrowly restrict, the channel 93. As seen therefore, the resilient or biasing member 17 has a first portion 95 of the channel 93 which receives the projection 34 when the ligating slide is in the first position 75; and a second portion of the channel 96 which receives the projection 34 when the ligating slide is in the second position 76. Therefore, the pair of members 84 and 85 resiliently cooperate with the outwardly or exterior facing surface 36 of the projection 34 to appropriately position and releasably restrain the ligating slide 16 in either of the first or second positions 75 and 76, respectively. The projection 34 passes along the channel when a clinician exerts sufficient force on the ligating slide 16 by means of an instrument, not shown, so as to cause projection 34 to biasingly move the members 84 and 85 apart so as to permit the projection 34 to pass along the passageway 93 to the appropriate location. As seen in FIGS. 3 and 5, for example, the projection 34 is operable to move along the channel 93 and between the first and second portions 95 and 96 thereof, to appropriately position the ligating gate 16 as described earlier. This arrangement is particularly advantageous inasmuch as the overall thickness dimension of the resulting first form of the orthodontic bracket 10 can be reduced thereby making the bracket more aesthetically appealing, and easier to fabricate. In addition to the foregoing, and in another possible form of the invention, it should be understood that the biasing member 80 may be made integral with the ligating slide 16. More specifically, the members 84 and 85 may be integrally molded with the ligating slide so as to provide the benefits discussed above.

Second Embodiment

The second embodiment of the orthodontic bracket of the present invention is generally indicated by the numeral 100 and is best seen by reference to FIGS. 11-17A, respectively. As seen therein, the second embodiment of the orthodontic bracket 100 is defined by a bracket body or base member 103 and which further defines a transversely disposed archwire slot 104 which is operable to receive an archwire 105 of traditional design. As earlier discussed, the archwire slot is shown in a transverse orientation relative to the bracket body or base member 103, however, it will be appreciated that the archwire slot 104 may be oriented in various orientations to achieve various clinical benefits for a patient. As seen in the drawings, the archwire slot 104 is substantially rectangular in shape, and is operable to receive a rectangular shaped archwire 105 of conventional design. The orthodontic bracket 100 includes a ligating slide 106 which moveably cooperates with the base member 103, and is moveable along a path of travel from a first position which allows access to the archwire slot 105 through the opening 108, and a second position where the moveable ligating slide 106 prevents access to the archwire slot. It will be appreciated by a study of FIG. 12 that the ligating slide 106 is resiliently deformable so as to facilitate passive self-ligation and the proper seating of the archwire 105 in the archwire slot 104. As should be understood, the present resiliently deformable ligating slide 106 may be sufficiently deformed such that it may close over an archwire 105 which may be slightly protruding from the archwire slot 104. Over time, however, the ligating slide 108 will assume its original shape to confine or otherwise enclose the archwire 105 within the archwire slot in the manner of passive self ligation, as earlier discussed. As seen by reference to FIG. 17, a planar resilient biasing member 107 is made integral with the moveable ligating slide and which is operable to biasingly position the moveable ligating slide 106 in one of the aforementioned positions relative to the archwire slot 104. As seen by reference to FIG. 12 and following, the base member 103 has an anterior facing surface or side 110, and an opposite posterior facing surface or side 111 which may be adhesively affixed, at least in part, to an underlying tooth of a patient who is being treated. Still further, the base member 103 has a top or superior facing surface 112, and a bottom or inferior facing surface 113. As seen in FIG. 12, the base member 103, and a portion of the moveable ligating slide 106 define individually elongated channels 114 which may be utilized to engage other orthodontic appliances as is customary for the treatment of a patient. The base member and ligating slide each respectively define a substantially continuous tie wing.

As seen in FIGS. 11 and 12, for example, and similar to the first form of the invention 10, a transverse substantially rectangular cross-sectioned passageway 120 is formed in the base member 103, and disposed in substantially parallel spaced relation relative to the archwire slot 104. As earlier disclosed, this transverse passageway 120 may receive other orthodontic appliances, such as a secondary archwire, or further may utilize a novel torquing spring or assembly 121 which is similar to that earlier disclosed, and which was described by reference to FIG. 19. In this regard, the torquing assembly 121 has a first portion 122 having a rectangular shape and which is dimensioned to be matingly received in the transverse passageway 120; and a second portion 123 which is attached to the first portion by an intermediate portion 122A. The intermediate portion is longitudinally, resiliently deformable by means of the second portion 123, and which can be rotated in a given direction, and thereafter forcibly engage the archwire 123 as seen in FIG. 13 in order to provide a torquing force on same to facilitate the movement of a tooth in a given direction. As seen in the drawings, the second form of the orthodontic bracket 100 includes a projection 124 (FIG. 12) which is received in a bore 125, and which extends generally posteriorly outwardly relative to the base member 103. The projection 124 has an exterior facing surface 126 which cooperates with the resilient biasing member 107 in order to achieve the benefits which will be discussed in greater detail hereinafter. As seen in FIG. 12, the bore 125 does not extend through the base member 103. Further, and when assembling the second form of the invention, it should be clear from a study of FIG. 12 that the projection 124 is inserted in the bore 125 from the posterior facing surface or side 11 of the base member 103. As seen by reference to FIGS. 12 and 17, respectively, the base member 103 further defines a substantially vertically oriented passageway 127 which slideably receives a portion of the moveable ligating slide 106, as will be discussed in greater detail, hereinafter. The vertically oriented passageway 127 has a first end 128, which is adjacent to the superior side of the base member 103, and a second end 129 which is adjacent to the inferior side of the orthodontic bracket 100. As seen by reference to FIG. 12, the projection 124 extends into and partially occludes the vertically oriented passageway 127. The operation of the passageway, in combination with the moveable ligating slide 107, will be discussed in greater detail, hereinafter.

As best seen by reference to FIGS. 17 and 17A, the base member 103 includes a pair of anteriorly extending guide members 130 which are positioned in predetermined substantially parallel spaced relation one relative to the other. The guide members 130 are operable to cooperate with the ligating slide 106 as will be described below. Each of the guide members have an inwardly facing surface 131 which defines a passageway 132 therebetween, and which slideably receives a portion of the ligating slide 106. Referring now to FIG. 17 and similar to the first form of the invention 10, the guide members each have a portion 134 which is operable to slideably restrain, and otherwise shield, at least in part, the ligating slide 106. this structural element is eliminated in the form of the invention as seen in FIG. 17A. As seen in FIGS. 17 and 17A, for example, the ligating slide 106 has a main body 150 having a first superior end 151, and an opposite second inferior end 152. The main body further has an anterior facing surface 153, and an opposite posterior facing surface 154. As seen in FIG. 12, a portion of the posterior facing surface 154 defines, in part, the archwire slot when the ligating slide is positioned in covering relation relative to the archwire slot to restrict access to same. The main body 150 has opposite substantially vertically disposed edges 155 and 156, respectively. Still further, the main body has a first portion 157 which forms, at least in part, a portion of the anterior facing surface 153 of the base member 103; and further, a second portion 158 is positioned in adjacent spaced relation relative to the posterior facing surface 111 of the base member. As seen in FIGS. 17 and 17A, the second portion 158 of the ligating slide 106 is disposed in spaced relation relative to the posterior facing surface 154. Still further, the second portion 158 is dimensioned, in length, thickness and width, to be slideably received within the vertically oriented passageway 127 which is defined by the base member 103. The second portion 158 of the ligating slide has integrally formed therewith, the planar resilient biasing member 107 as will be described in greater detail, hereinafter. As with the first form of the invention 10, the resilient biasing member 107 defines a course of movement for the accompanying ligating slide 106 for the purposes which will be described below. As seen in FIGS. 14 and 17, the ligating slide 106 further defines first and second recessed regions 159A and B, respectively. As illustrated, these recessed regions have a thickness dimension which allows the ligating slide to be slideably received therebetween the portions 134 and base member 103 so as to facilitate the reciprocal sliding movement of the ligating slide 106, as described below. As best see by reference to FIG. 17A, an alternative second form of the invention is shown. In this regard, it will be seen that the ligating slide has been modified to eliminate the recessed regions 159A and B, respectively. Further, and as noted above, the guide members 130 have been modified to eliminate the structural element 134, (FIG. 17) which was operable in the previous form of the invention, to restrain the movement of the ligating slide 106.

Referring now, for example, to FIGS. 17 and 17A, it will be understood that the second form of the orthodontic bracket 100 includes a substantially planar resilient biasing member 107 which is made integral with the second portion 158 of the ligating slide 106, and which further resiliently cooperates, and receives, the projection 124 which extends posteriorly, rearwardly, and into the passageway 127 which is defined by the base member 103. Similar to the resilient biasing member 80 as described with the first form of the invention 10, the resilient biasing member 107 has a main body 160 which has a transverse portion 161. The transverse portion has opposite first and second ends 162 and 163 which are made integral with the second portion 158 of the ligating slide 106. The main body of the planar resilient biasing member 160 further includes first and second depending members 164 and 165 which are each disposed in predetermined, spaced relation one relative to the other. Each of the depending members 164 and 165 have a distal end 170, and have an outwardly facing edge 171, and an opposite, inwardly facing edge 172 which defines a channel 173, therebetween. As seen in the drawings, a portion of each of the inwardly facing surfaces define a biasing abutment 174 which occludes, at least in part, the channel 173. In this regard, the channel 173 is defined by a first portion 175 which, when the projection 124 is received therein, positions the ligating slide in a position whereby a practitioner can gain access to the archwire slot 104, and a second portion 176, whereby the resilient biasing members resiliently secures the ligating slide 106 in a substantially closed position thereby restricting access to the archwire slot 104 and capturing the archwire 105 therein. This is seen by a study of FIGS. 11 and 13, respectively. As seen in FIG. 16, the first and second depending legs are resiliently moveable laterally outwardly, one relative to the other to allow for the passage of the projection 124 therethrough, thereby locating the projection 124 in either the first or second portions 175 and 176 of the channel 173. As seen from a study of FIGS. 11 and 13, the ligating slide 106 is moveable along a course of travel or movement 180, between a first position 181, where the ligating slide 106 allows access to the archwire slot 104 (FIG. 13), and wherein the projection 124 is in engagement thereagainst the transverse portion 161; and a second position 182, and where the ligating slide 106 projects over the opening 108 and restricts access to the archwire slot 104 (FIG. 11). In this arrangement, the ligating slide 106 is biasingly supported in at least one of the first or second positions by the planar biasing member 107. As seen by reference to FIGS. 11 and 13, the first portion 175 of the channel 173 receives the projection 124 when the ligating slide is in the first position 181 (FIG. 13), and the second portion 176 receives the projection 124 when the ligating slide 106 is in the second position 182. As similarly described with respect to the first form of the invention, the biasing force applied to the biasing member 107 is substantially perpendicular relative to the projection 124 and substantially parallel to the path of movement 180 of the ligating slide 106.

Third Embodiment

Figure 20:
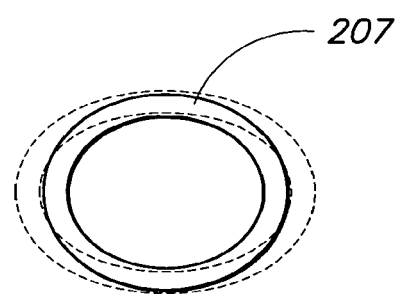
FIG. 20 is a top plan view of one form of a biasing member which is useful in the third form of the orthodontic bracket of the present invention.

The third embodiment of the orthodontic bracket of the present invention is generally indicated by the numeral 200, and is best seen by reference to FIG. 18. As seen therein, the third embodiment of the orthodontic bracket 200 is defined by a bracket body or base member 203 and which further defines a transversely disposed archwire slot 204 which is operable to receive an archwire 205 of traditional design. As earlier discussed with respect to the first and second forms of the invention, the archwire slot 204 is shown in a transverse orientation relative to the bracket body or base member 203, however, it will be appreciated that the archwire slot 204 may be located in various orientations to achieve assorted clinical benefits for a patient. As seen in FIG. 18, the archwire slot 204 is substantially rectangular and is operable to receive a rectangular shaped archwire 205 of conventional design. The orthodontic bracket 200 further includes a ligating slide 206 which moveably cooperates with the base member 203, and is moveable along a path of travel from a first position which allows access to the archwire slot 204 through an opening 208, and a second position, where the moveable ligating slide 206 prevents access to the archwire slot. Similar to that described with respect to the forms of the invention which were earlier described, it will be understood that the ligating slide 206 is resiliently deformable so as to facilitate passive self-ligation, and the proper seating of the archwire 205 in the archwire slot 204, if necessary. The ligating slide is shown in phantom view in order to illustrate the relative resiliency and movement of the ligating slide relative to the bracket body or base member 203. As seen in FIGS. 18 and 20, the third embodiment or form of the invention 200 includes a biasing member 207 which is borne by the base member 203, and which resiliently cooperates with a portion of the ligating slide 206. As seen in FIG. 18, the biasing member 207 exerts a biasing force which is directed posteriorly outwardly relative to the base member 203 to position the ligating slide 206 in the opposite first and second positions which are shown, alternatively, in solid as well as in phantom lines. As will be recognized from a study of FIG. 18, the biasing member 207 is carried by, or otherwise positioned, mounted, or received within a portion of the base member 203 as will be described in further detail below. The biasing member 207 is operable to releasably biasingly position the moveable ligating slide 206 in one of the aforementioned positions relative to the archwire slot 204. As seen in FIG. 18, the base member 203 has an anterior facing surface or side 210; and an opposite posterior facing surface or side 211 which may be adhesively affixed, at least in part, to an underlying tooth of a patient who is being treated. Still further, the base member 203 has a top or superior facing surface or portion 212, and a bottom, lowermost or inferior facing surface 213. Similar to that described with the first and second forms of the invention, the base member as well as the moveable ligating slide 206 define individual elongated channels 214 which may be utilized to engage other orthodontic appliances as is customary for the treatment of a patient. As earlier described, this arrangement results in an orthodontic bracket which has substantially continuous superior and inferior tie wings.

Figure 19:
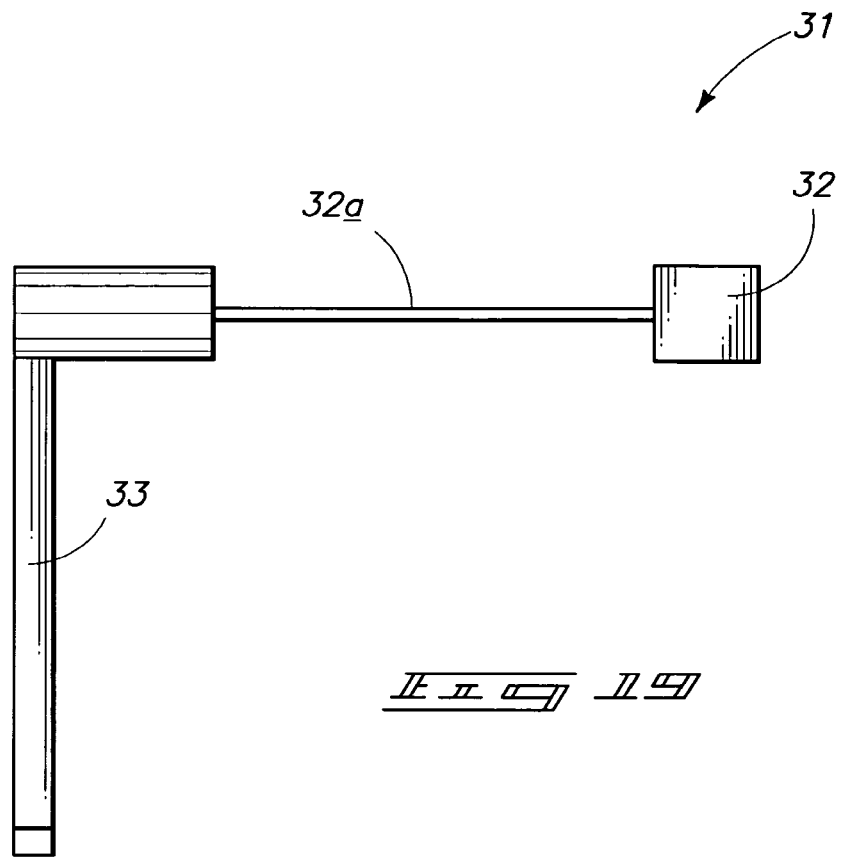
FIG. 19 is a side elevation view of an orthodontic appliance employed with the various forms of the orthodontic bracket of the present invention.

As seen in FIG. 18, and similar to the earlier forms of the invention, a transverse, substantially rectangular cross-sectional passageway 220 is formed in the base member 203 and disposed in substantially parallel, spaced relation relative to the archwire slot 204. This transverse passageway 220 may receive other orthodontic appliances such as a secondary archwire, or further may utilize a novel torquing spring assembly such as what is seen in FIG. 19 and which was earlier described with respect to the first and second forms of the invention. As seen in FIGS. 18 and 20, and as discussed briefly above, the second form of the invention 200 includes a biasing member 207 which exerts a biasing force which is directed generally posteriorly outwardly relative to the base member 203 to position the ligating slide 206 in the first and second positions, as described earlier. In this regard, the biasing member 207 is carried or otherwise positioned or mounted on the base member 203 and is typically received within a cavity 221 that is formed therein. As seen from FIG. 18 it will be understood that the cavity 221 does not extend through the base member. Further, it should be appreciated that the biasing member 207 can take on a number of configurations. Some possible configurations are those which are illustrated in U.S. Pat. No. 5,466,151, the teachings of which are incorporated by reference herein. One possible form of the biasing member is seen in FIG. 20 where the biasing member is illustrated as a deformable, resilient o-ring which is fabricated of a metal and/or composite and which is received in the cavity 221. As will be appreciated, force applied to the o-ring causes it to resiliently deform so as to permit the movement of the ligating slide 206. As further seen by reference to FIG. 18, the base member 203 further defines a substantially vertically oriented passageway 222 which slideably receives a portion of the moveable ligating slide 206 as will be discussed below. The vertically oriented passageway 222 has a first end 223 which is adjacent to the superior side of the base member 203, and a second end 224 which is adjacent to the inferior side of the orthodontic bracket 200. As illustrated in FIG. 19, the biasing member 207 extends into and partially occludes the vertically oriented passageway 222. The operation of this passageway in combination with the moveable ligating slide 206 will be discussed in greater detail, below.

As seen in FIG. 18, the ligating slide 206 has a main body 230 having a first superior end 231, and an opposite inferior end 232. The main body further has an anterior facing surface 233; and an opposite posterior facing surface 234. In the drawing, it will be seen that a portion of the posterior facing surface defines, at least in part, the archwire slot 204 when the ligating slide 206 is positioned in covering relation relative to the archwire slot or opening 208 to restrict access to same. In addition to the foregoing, the main body 230 defines a first portion 237 which forms, at least in part, a portion of the anterior facing surface 233 of the base member 203; and further a second portion 238 which is positioned in adjacent spaced relation relative to the posterior facing surface 211 of the base member 203. As seen in FIG. 18, the second portion 238 of the ligating slide 206 is disposed in spaced relation relative to the anterior facing surface 233 and the first portion 237. Still further, the second portion 238 is dimensioned in length, thickness, and width so as to be slideably received within the vertically oriented passageway 222 which is defined by the base member 203. As seen in the present drawing, the second portion 238 has formed therein a plurality of detents, cavities or receiving regions 239 and which receive or otherwise cooperate with a portion of the biasing member 207 so as to releasably position the ligating slide 206 in the first and second positions, as will be discussed below.

As seen from a study of FIG. 18, the ligating slide 206 is moveable along a course of travel 240, from a first position 241 and wherein the biasing member 207 is received, at least in part, and cooperates with one of the detents, cavities, or receiving regions 239, and wherein the ligating slide (phantom lines) and more specifically the first portion 237 thereof allows access to the archwire slot 204; and a second position 242 (solid lines) and wherein the ligating slide 206 and more specifically the first portion thereof projects over the opening 208 and otherwise substantially restricts access to the archwire slot 204. In the second position 242, again the biasing member 207 is received in one of the detent or receiving regions 239 in order to releasably secure the ligating slide 206 in the appropriate position. To move the ligating slide between the second and first positions, a clinician would merely insert an instrument in the passageway 222 and more specifically at the first end 223 thereof and press downwardly on the second portion 238 of the ligating slide 206 which is slideably received within the passageway 222.

Therefore in the third form of the invention, an orthodontic bracket 200 is described and which includes a base member 203 having anterior and posterior facing surfaces 210 and 211, respectively and further defining an archwire slot 204 having an opening 208 in the anterior facing surface 210. Still further, in this third form of the invention, a ligating slide 206 is movably borne by the base member 203 between a first position 241 which is clear of the archwire slot 204; and a second position 242, where the ligating slide 206 projects over the archwire slot. Still further, a biasing member 207 is provided, and which is borne by the base member 203, and which resiliently cooperates with the ligating slide 206. As illustrated, the biasing member 207 exerts a biasing force which is directed posteriorly outwardly relative to the base member 203 to position the ligating slide in the first and second positions 241 and 242, respectively. As earlier noted, a cavity 221 is formed in the base member 203 and which receives, at least in part, the biasing member 207. As with the other several forms of the invention as earlier described, the first portion 237 of the ligating slide 206 is resiliently deformable so as to further facilitate passive self-ligation if necessary.

Fourth Embodiment

Figure 23:
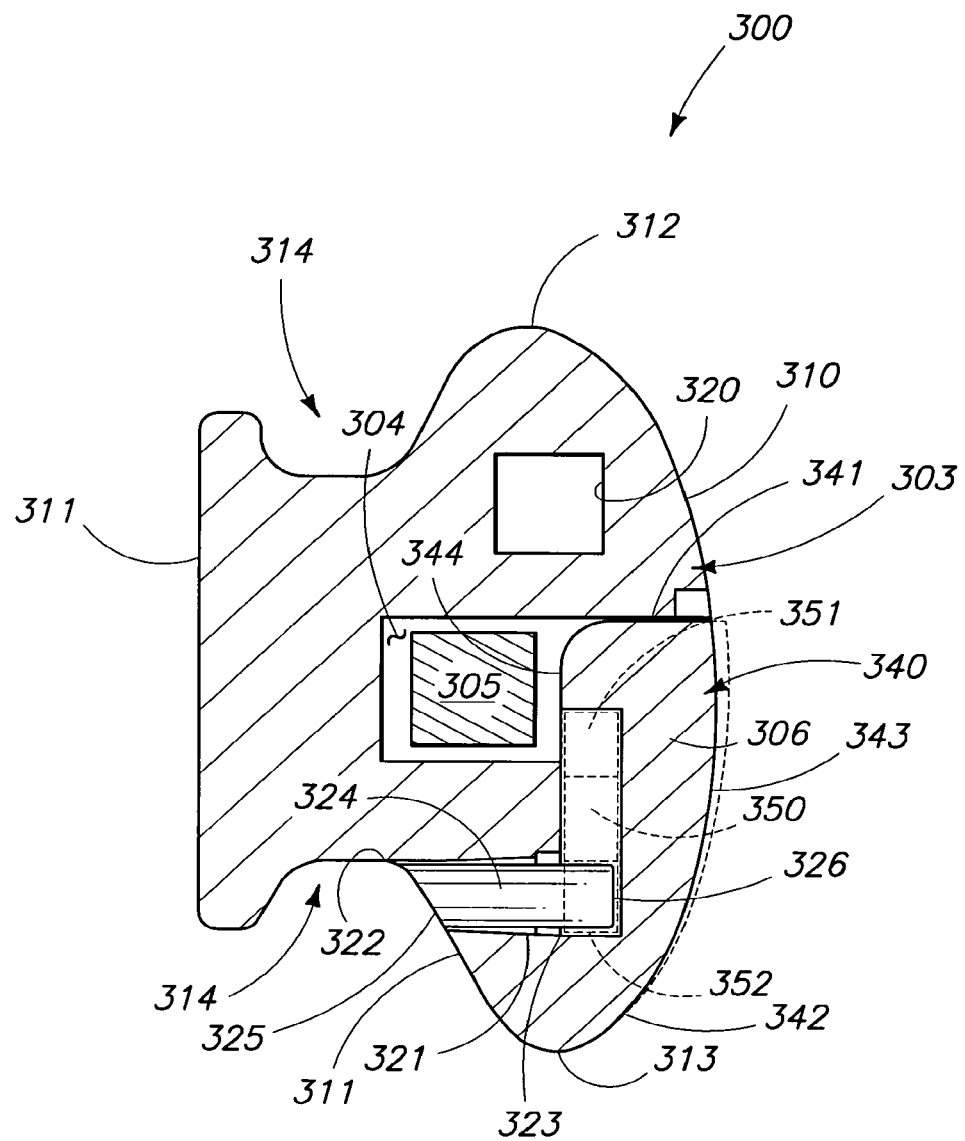
FIG. 23 is a transverse, vertical sectional view of the fourth form of the orthodontic bracket of the present invention, and which is taken from a position along line 23-23 of FIG. 22.

The fourth embodiment of the orthodontic bracket of the present invention is generally indicated by the numeral 300, and is best understood by a study of FIGS. 21-25, respectively. As seen therein, the third embodiment of the orthodontic bracket 300 is defined by a bracket body or base member 303 and which further defines a transversely disposed archwire slot 304 which is operable to receive an archwire 305 of traditional design. As discussed with respect to the first, second and third forms of the invention, the archwire slot is shown in a transverse orientation relative to the bracket body or base member 303. It will be appreciated, however, that the archwire slot 305 may be oriented in various orientations to achieve assorted clinical benefits for a patient. As will be appreciated from a study of FIG. 23, the archwire slot 304 is substantially rectangularly shaped and is operable to receive a rectangular or square shaped archwire 305 of conventional design. The orthodontic bracket 300 further includes a ligating slide 306 which moveably cooperates with the base member 303, and is moveable along a path of travel from a first position which allows access to the archwire slot 304 through an opening 308; and a second position, where the moveable ligating slide 306 prevents access to the same archwire slot. Similar to that described with respect to the other forms of the invention, it will be understood that the ligating slide 306 is resiliently deformable so as to facilitate passive self-ligation and the proper seating of the archwire 305 in the archwire slot 304, if necessary. As seen in FIG. 23, the ligating slide is shown in phantom view in order to illustrate the relative resiliency and movement of the ligating slide relative to the bracket body or base member 303.

Figure 21:
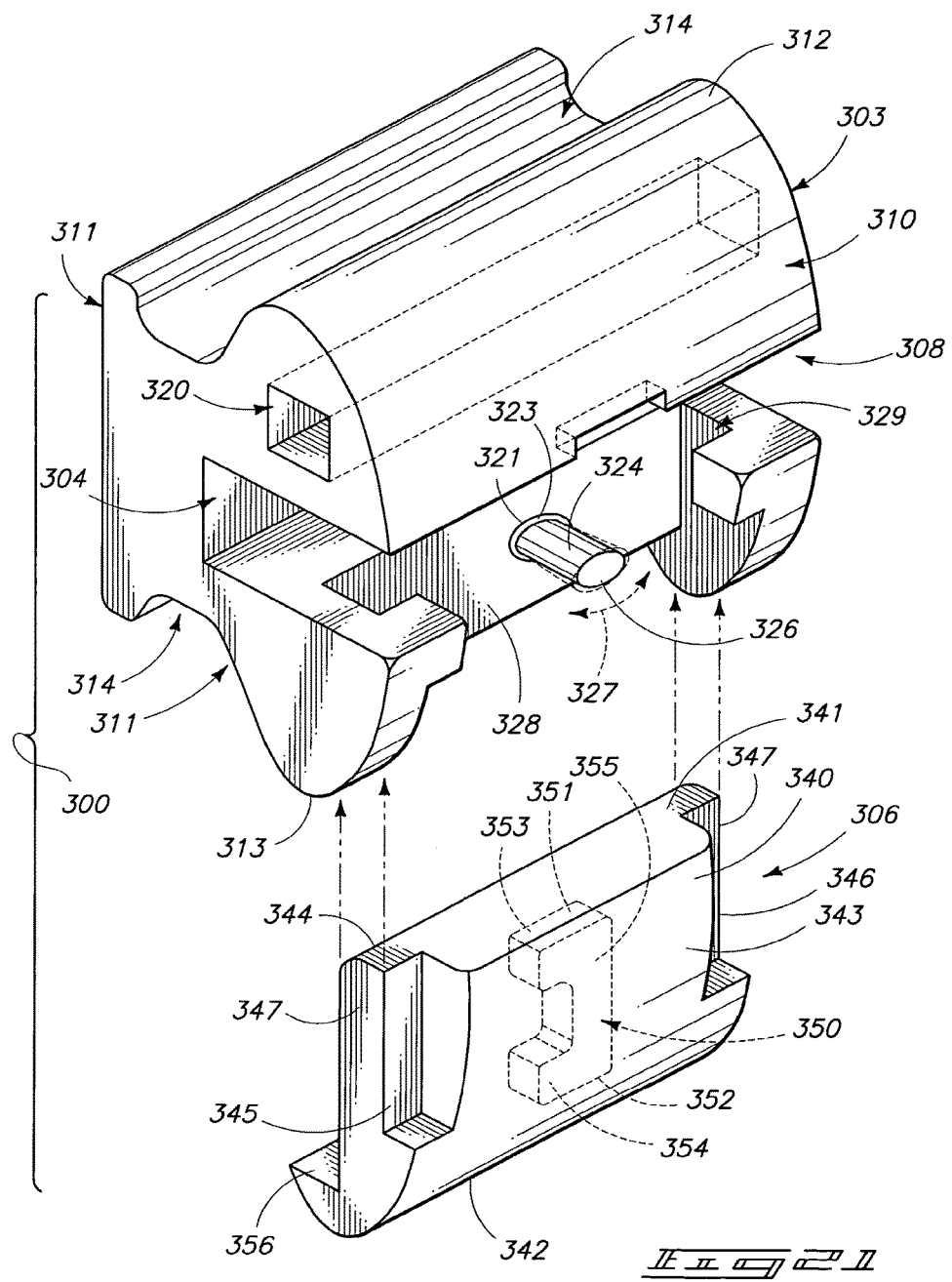
FIG. 21 is a perspective, exploded, front elevation view of fourth form of the orthodontic bracket of the present invention. Some underlying surfaces are shown in phantom lines.
Figure 22:
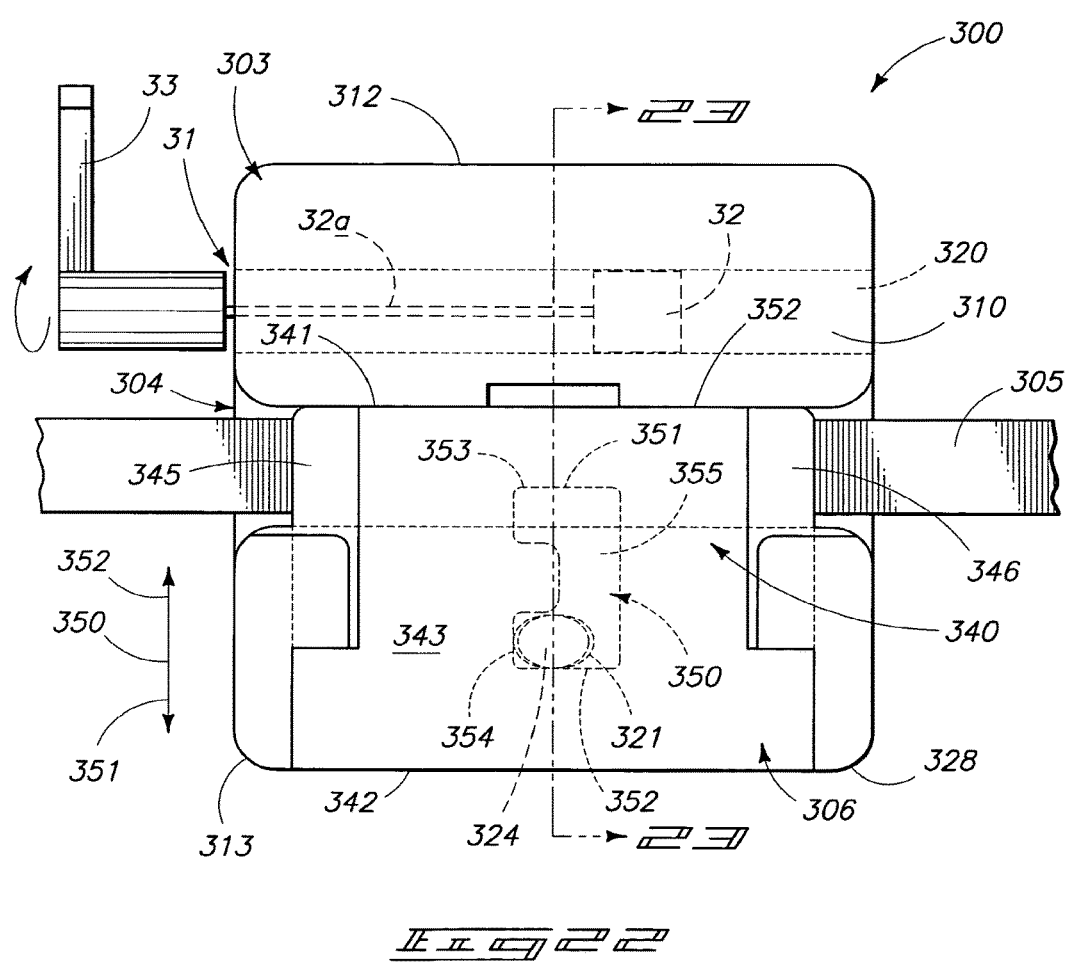
FIG. 22 is a greatly enlarged, front elevation view of the fourth form of the orthodontic bracket of the present invention.

As best seen by reference to FIG. 21, the base member 303 has an anterior facing surface or side 310, and an opposite posterior facing surface or side 311. the posterior facing surface may be adhesively affixed, at least in part, to an underlying tooth of a patient who is being treated. Still further, the base member 303 has a top or superior facing surface or portion 312, and a bottom, lowermost or inferior facing surface 313. Similar to that described with respect to the first, second and third forms of the invention, the base member 303 as well as the moveable ligating slide 306 define individually elongated channels 314 which may be utilized to engage other orthodontic appliances as is customary for the treatment of a patient. As earlier described, this arrangement results in an orthodontic bracket which has substantially continuous superior and inferior tie-wings.

As seen in FIG. 21 and following, and similar to the earlier forms of the invention, a transverse, substantially rectangular cross-sectional shaped passageway 320 is formed in the base member 303 and is disposed in substantially parallel spaced relation relative to the archwire slot 304. This transverse passageway 320 may receive other orthodontic appliances such as secondary archwire or further may utilize a novel torquing spring assembly as was previously described with respect to FIG. 19; or a hook as seen in FIG. 3A and which is generally designated by the numeral 38.

As seen in FIG. 21 and following, it should be understood, that a bore 321 is formed in the base member 303, and more specifically in the lowermost or inferior surface 313 thereof. The elongated bore has a first end 322 which is located adjacent to the posterior facing surface 311 of the base member 303; and further has a second end 323 which is located adjacent to the anterior facing surface 310 as seen most easily by reference to FIG. 21. As best understood by reference to FIG. 23, it should be understood that the bore has a diametral dimension which generally increases when measured from the posterior facing surface 311 in the direction of the anterior facing surface 310. More specifically, and as seen in FIG. 23, it will be recognized, that the inside diametral dimension, at the second end 323, is greater than the outside diametral dimension of an elongated flexible projection or member 324 which is received in same. This relationship allows the elongated flexible projection or member 324 to move relative to the bore. This will be discussed in greater detail below.

As seen in FIG. 23, it will be appreciated that the fourth form of the invention 300 includes an elongated flexible projection or member 324 which has a proximal end 325 which is located near and otherwise affixed to the posterior facing surface 311 of the base member 303. Still further, the flexible projection or member 324 has a distal end 326 which extends anteriorly, outwardly relative to the anterior facing surface 310 of the base member 303. As illustrated most clearly to reference to FIG. 21, the distal end 326 is operable to move along an arcuately shaped path of travel 327 when the ligating slide 306 moves between the first open position where the ligating slide 306 is clear of the archwire slot 304; and the second position where the ligating slide restricts access or otherwise projects over the archwire slot. Therefore, in one aspect of the present invention, an orthodontic bracket 300 is disclosed and which includes a base member 303 defining an archwire slot 304; and an elongated flexible member 324 is borne by the base member and which has a distal end 326 which is moveable along an arcuately shaped path of travel 327. Still further in this form of the invention, a ligating slide 306 is moveably borne by the base member 303 between a first position where the ligating slide is clear of the archwire slot 304; and a second position where the ligating slide restricts access to the archwire slot. In this regard, the distal end 326 of the elongated flexible member 324 cooperates with the ligating slide 306 and moves along the arcuately shaped path of travel as the ligating slide moves between the first and second positions. As will be appreciated from a study of the drawings, the arcuately shaped path of travel 327 (which is greatly exaggerated to reveal this feature of the invention) is generally parallel to the anterior facing surface 310 of the base member 303. In view of the arrangement of the bore 321, as earlier described, the arcuately shaped path of travel 327 of the distal end 326 is generally facilitated. However, it should be understood that the flexible member 324 as herein described is not deformable or compressible in a longitudinal direction as was previous prior art assemblies. Rather, as seen in the drawings, the flexible member merely is operable to allow the distal end 326 thereof to move along the arcuately shaped path of travel for the benefits that will be described hereinafter. As illustrated most clearly by reference to FIG. 21, the base member has a lowermost portion 328 which defines a channel 329 which extends from the archwire slot 304 to the lowermost portion. As seen in the drawings, and as appreciated from the various views, the ligating slide 306 is slideably received in the channel defined by the base member, and the elongated flexible projection or member 324 defines the path of travel for the ligating slide as it moves between the first open position which is clear of the archwire slot, to the second position where the ligating slide 306 projects over the archwire slot and restricts access to same.

As best illustrated by reference to FIG. 21, the ligating slide 306 has a main body 340 having a first superior end 341, and an opposite inferior end 342. The main body further has an anterior facing surface 343 and an opposite posterior facing surface 344. In the drawings as provided, it will be seen that a portion of the posterior facing surface defines, at least in part, the archwire slot 304, and the ligating slide 306 is positioned in covering relation relative to the archwire slot or opening 308 to restrict access to same. In addition to the foregoing, the main body, and more specifically, the anterior facing surface 343 thereof has a first recessed region 345 and a second recessed region 346 formed therein. These recessed regions allow the ligating slide 306 to be matingly received in the channel 329, and move along a course of travel which will be discussed in greater detail hereinafter. As best seen by reference to FIG. 21 and following, a channel 350 having a given nonlinear shape is formed in the posterior facing surface 344 of the main body 340 and is operable to receive the distal end 326 of the flexible projection or member 324. As seen therein, the channel has a first end 351, and a second, opposite end 352. Still further, there is a first transversely disposed seat 353 formed at the first end 351, and a second, transversely disposed seat 354 formed at the second end thereof. The channel includes an intermediate portion 355 which couples the first and second transverse seats 353 and 354 together. Still further, the main body 340 includes an abutting edge 356. As should be understood, the ligating slide 306 is slideably borne by the base member 303, and is moveable between a first, open position which allows access to the archwire slot 304 and a second closed position which restricts access to the archwire slot. The ligating slide 306 has an anterior and a posterior facing surface 343 and 344, respectively, and wherein a channel 350 is formed in the posterior facing surface of the ligating slide and is operable to receive the elongated flexible member 324 therein. As earlier discussed, the flexible member has a distal end 326 which is received in the channel and wherein the distal end is resiliently deformed along a substantially arcuately shaped path of travel 327. The flexible member cooperates with the channel 350 to releasably secure the ligating slide 306 in the first and second positions as will be described below. In the arrangement as seen in the drawings, the channel 350 includes first and second transverse seats 353 and 354, respectively, which are located at the first and second ends 351 and 352 of the channel. These individual seats are each dimensioned to matingly receive the flexible projection or member 324 and wherein the flexible projection or member is not substantially deformed when received in the respective seats. As should be understood, the movement of the ligating slide 306 between the first and second positions causes the flexible projection or member to resiliently deform and move out of the respective seats and along the intermediate portion 355 of the channel. As will be recognized from a study of FIG. 23, and similar to the previous forms of the invention, the ligating slide 306 is resiliently deformable and has a superior end 341 which is rounded or beveled, at least in part. Still further, the ligating slide 306 has opposite peripheral edges 347 and the base member 303 shields, at least in part, the opposite peripheral edges as best seen by reference to FIG. 22.

As seen from a study of the drawings, the ligating slide 306 is moveable along a course of travel 350 from a first position 351 and wherein the distal end 326 of the elongated flexible projection or member is received in the first transverse seat 353 which is located at the first end of the channel 350, and wherein the ligating slide is substantially clear of the archwire slot 304; and a second position 352, and wherein the distal end 326 is located at the second seat 354 and the ligating slide 306 is located in substantially covering relation over the archwire slot and thereby inhibits access to same.

Fifth Embodiment

The fifth embodiment of the orthodontic bracket of the present invention is generally indicated by the numeral 400, and is best seen by reference to FIGS. 26 and 27, respectively. As seen therein, the second embodiment of the orthodontic bracket 400 is defined by a bracket body or base member 403 and which further defines a transversely disposed archwire slot 404 which is operable to receive an archwire 405 of traditional design. As earlier discussed, the archwire slot 404 is shown in a transverse orientation relative to the bracket body or base member 403, however, it will be appreciated that the archwire slot 404 may be oriented in various orientations to achieve various clinical benefits for a patient. As seen in the drawings, the archwire slot 404 is substantially rectangular in shape, and is operable to receive a rectangular or square shaped archwire 405 of conventional design. The orthodontic bracket 400 includes a ligating slide 406 which moveably cooperates with the base member 403, and is moveable along a path of travel from a first position which allows access to the archwire slot 405 through the opening 408, and a second position where the moveable ligating slide 406 prevents access to the archwire slot. It will be appreciated by a study of FIG. 27 that the ligating slide 406 is resiliently deformable so as to facilitate passive self-ligation, and the proper seating of the archwire 405 in the archwire slot 404. As should be understood, the present resiliently deformable ligating slide 406 may be deformed sufficiently such that it may close over an archwire 405 which may be slightly protruding from the archwire slot 404. Over time, however, the ligating slide 408 will assume its original shape to confine or otherwise enclose the archwire 405 within the archwire slot in the manner of passive self ligation, as earlier discussed. As seen by reference to FIGS. 26 and 27, the base member 403 has an anterior facing surface or side 410, and an opposite posterior facing surface or side 411, which may be adhesively affixed, at least in part, to an underlying tooth of a patient who is being treated. Still further, the base member 403 has a top or superior surface 412, and a bottom or inferior surface 413. As seen in FIG. 27, the base member 403, and a portion of the moveable ligating slide 406 define individually elongated channels 414 which may be utilized to engage other orthodontic appliances as is customary for the treatment of a patient. The base member and ligating slide each define a substantially continuous tie wing.

As seen in FIGS. 26 and 27, for example, and similar to the other forms of the invention, a transverse substantially rectangular cross-sectioned passageway 420 is formed in the base member 403, and is disposed in substantially parallel spaced relation relative to the archwire slot 404. As earlier disclosed, this transverse passageway 420 may receive other orthodontic appliances, such as a secondary archwire, or further may utilize the novel torquing spring assembly 31 such as described in previous forms of the invention, and which is seen in FIG. 19. As seen in the drawings, the fifth form of the orthodontic bracket 400 includes an elongated flexible member 424 which is received in a bore 425, and which extends generally posteriorly outwardly relative to the base member 403. The flexible member has a proximal end 426 which is secured in the base 425, and a distal end 427 which cooperates with the ligating slide 406 in order to achieve the benefits which will be discussed in greater detail hereinafter. As seen in FIG. 27, the bore 425 does not extend through the base member 403 and has variable diametral dimension which facilitates the movement of the distal end 427 along an arcuately shaped path of travel similar to that disclosed in the fourth form of the invention. Further, and when assembling the fifth form of the invention, it should be clear from a study of FIG. 27 that the flexible member 424 is inserted in the bore 425 from the posterior side 411 of the base member 403. It is, of course, possible to fabricate a base member where the flexible member could be inserted from the anterior facing surface thereof. As seen by reference to FIGS. 26 and 27, respectively, the base member 403 further defines a substantially vertically oriented passageway 428 which slideably receives a portion of the moveable ligating slide 406 as will be discussed in greater detail hereinafter. The vertically oriented passageway is located adjacent to the posterior facing surface 411 and extends from the superior surface 412 of the base member 403 to the inferior 413. As seen by reference to FIG. 27, the projection 424 extends into and partially occludes the vertically oriented passageway 428. The operation of the passageway, in combination with the moveable ligating slide 406, will be discussed in greater detail, hereinafter.

As best seen by reference to FIGS. 26 and 27, the base member 403 includes a pair of anteriorly extending guide members 430 which are positioned in predetermined substantially parallel spaced relation one relative to the other. The guide members 430 are operable to cooperate with the ligating slide 406 as will be described below. Each of the guide members have an inwardly facing surface 431 which defines a passageway 432 therebetween, and which slideably receives a portion of the ligating slide 406. Further, and similar to the other forms of the invention 10, the guide members may further include a portion which is operable to slideably restrain, and otherwise shield, at least in part, the ligating slide 106 (not shown in FIG. 26). As seen in FIGS. 26 and 27, for example, the ligating slide 406 has a main body 450 having a first superior end 451, and an opposite second inferior end 452. The main body further has an anterior facing surface 453, and an opposite posterior facing surface 454. As seen in those drawings, a portion of the posterior facing surface defines, in part, the archwire slot 404 when the ligating slide is positioned in covering relation relative to the archwire slot to restrict access to same. Such as seen in FIG. 27. The main body 450 has opposite substantially vertically disposed peripheral edges 455 and 456, respectively. Still further, the main body has a first portion 457 which forms, at least in part, a portion of the anterior facing surface 453 of the base member 403; and further, a second portion 458 which is positioned in adjacent spaced relation relative to the posterior facing surface 411 of the base member when the orthodontic bracket 400 is assembled. As seen in FIGS. 26 and 27, the second portion 458 of the ligating slide 406 is disposed in spaced relation relative to the posterior facing surface 454. Still further, the second portion 458 is dimensioned, in length, thickness and width, to be slideably received within the vertically oriented passageway 428 which is defined by the base member 403. The second portion of the ligating slide defines a channel 459 similar in shape and in function as was previously described with respect to the earlier forms of the invention and which receives the distal end 427 of the flexible member 426. The flexible member, in cooperation with the channel 459 defines a course of movement for the accompanying ligating slide 406 for the purposes which will be described, below.

As seen from a study of FIGS. 26 and 27, the ligating slide 406 is moveable along a course of travel or movement between a first position, where the ligating slide 406 allows access to the archwire slot 404, and wherein the flexible member 424 is at one end of the channel 459, and a second position where the ligating slide 406 projects over the opening 408 and restricts access to the archwire slot 404 (FIG. 27), and the flexible member 424 is at the opposite end of the channel 459. As the flexible member moves along the channel, the distal end thereof moves along the arcuately shaped path of travel as was previously described in the earlier forms of the invention. In this arrangement, the ligating slide 406 is biasingly supported in at least one of the first or second positions by the flexible member 424.

Operation

The operation of the described embodiments of the present invention are believed to be readily apparent and are briefly summarized at this point.

In its broadest aspect, the present invention relates to an orthodontic bracket 10, 100, which includes a ligating slide 16, 106 which is configured to be coupled to a base member 13, 103 and wherein the ligating slide further cooperates F with a biasing member 17, 107 which receives, at least in part, a portion of the base. As illustrated, and in two forms of the invention 10 and 100, the biasing member exerts a biasing force which is directed principally in a direction which is substantially parallel, and in spaced relation relative to the direction, or path of movement of the ligating slide. Still further, the present invention relates to an orthodontic bracket 10, 100 which includes a base member 13, 103 defining an archwire slot 14, 104 having an opening 44, 108, and wherein at least one projection 34, 124 extends outwardly from the base member 13, 103. The orthodontic bracket 10, 100 further includes a ligating slide 16, 106 which is moveable along a course of travel between a first position 75, 181 which is clear of the archwire slot 14, 104 and a second position 76, 182 where the ligating slide 16, 106 projects over the opening 44, 108 of the archwire slot. Still further, the present invention includes a resilient biasing member 17, 107 borne by the ligating slide 16, 106 and slideably cooperating with a projection 34, 124, and wherein the resilient member has a first portion 95, 175 which receives the projection 34, 124 when the ligating slide is in the first position 75, 181 and a second portion 96, 176 which receives the projection 34, 124 when the ligating slide is in the second position 76, 182.

The orthodontic bracket 10, 100 of the present invention includes a base member 13, 103 defining a transverse archwire slot 14, 104 having an opening 44, 108. A ligating slide 16, 106 is borne by the base member 13, 103 and is further moveable relative to the archwire slot 14, 104, and wherein the ligating slide is moveable between a first position 75, 181 where the ligating slide allows access to the archwire slot, and a second position 76, 182 where the ligating slide projects over the opening 44, 108 and restricts access to the archwire slot 14, 104. In the present invention, the ligating slide 16, 106 is biasingly supported in at least one of the first or second positions as described above. As was described earlier, the biasing force supplied by the biasing member is generally in a direction which is substantially parallel to the direction of movement of the ligating slide.

The orthodontic bracket 10, 100 of the present invention further comprises, in one respect, a base member 13, 103 having a transverse archwire slot 14, 104 defining an opening 44, 108 and at least one projection 34, 124 extending outwardly from the base member 13, 103. The present invention further includes a ligating slide 16, 106 moveable between a first position 75, 181 which is clear of the archwire slot and a second position 76, 182 projecting over the opening of the archwire slot. Still further in the present invention, a substantially planar resilient biasing member 17, 107 is borne by the ligating slide 16, 106 and matingly cooperates with the projection 34, 124. In the arrangement as seen in the drawings, a first portion of the biasing member 95, 175 receives the projection when the ligating slide 16, 106 is in the first position 75, 181, and a second portion 96, 176 receives the projection 34, 124 when the ligating slide is in the second position.

The orthodontic bracket 10, 100 further comprises a base member 13, 103 having an opening 44, 108 and a transverse passageway 30, 120, which is oriented in substantially parallel spaced relation relative to the archwire slot 14, 104. Still further, the orthodontic bracket 10, 100 includes a ligating slide 16, 106 borne by the base member 13, 103 and moveable relative to the archwire slot 14, 104, and wherein the ligating slide is moveable between a first position 75, 181 where the ligating slide is clear of, and allows access to the archwire slot; and a second position 76, 182 where the ligating slide projects over, and restricts access to, the archwire slot 14, 104. As earlier disclosed, the transverse passageway 30, 120 is operable to cooperate with a torquing assembly 31, 121 in order to exert force upon an archwire 15, 105.

Another aspect of the orthodontic bracket 10, 100 of the present invention includes a base member 13, 103 having a posterior facing surface 21, 111 and an anterior facing surface 20, 110 and a projection 34, 124 extending outwardly from one or both of the posterior 21, 111 and/or anterior facing surfaces 20, 110, and wherein the projection 34, 124 has an outwardly facing surface 36, 126. A ligating slide 16, 106 is borne by the base member 13, 103, and further has a pair of members 84, 85, 164, 165 having opposing surfaces 92, 172 and a channel 93, 173 defined therebetween the opposing surfaces 92, 172. The channel defined by the biasing member is substantially parallel to the ligating slide. The pair of members 84, 85, 164, 165 resiliently cooperate with the outwardly facing surface 36, 126 of the projection 34, 124 in order to exert a biasing force which is substantially parallel to the direction of movement of the ligating slide, and which positions the ligating slide 16, 106 in an appropriate orientation relative to the archwire slot 14, 104. In this regard, the pair of members 84, 85, 164, 165 are spaced, and resiliently moveable, one relative to the other. Still further, a biasing abutment 94, 174 is defined by one of the surfaces 92, 172 of the respective members. The biasing abutment at least partially occludes the channel 93, 173.

The present invention also relates to an orthodontic bracket 100 which has a base member 103 having a posterior facing surface 111, and an anterior facing surface 110, and wherein a projection 124 extends generally outwardly and in the direction of the posterior facing surface 111, and wherein the anterior facing surface 110 of the base member 103 defines an archwire slot 104 having an opening 108. In this second form of the invention 100, a ligating slide 106 is borne by the base member 103 and is moveable along a course of travel 180 between a first position 181 which allows access to the archwire slot 104 through the opening 108, and a second position 182, which restricts access to the archwire slot 104 through the same opening 108. In this arrangement, the ligating slide 106 includes a first portion 157 which extends to a second portion 158. In this arrangement, the first portion 157 forms, at least in part, a portion of the anterior facing surface 110 of the base member 103, and the second portion 158 is positioned in adjacent spaced relation relative to the posterior facing surface 111 of the base member 103. In the arrangement as seen the second form of the invention 100, a resilient biasing member 107 is coupled to the ligating slide 106 and which operatively mates with and or otherwise cooperates with the projection 124. The resilient biasing member 107 exerts a biasing force relative to the projection 124 which is substantially perpendicular; and further substantially parallel and non-coaxial alignment relative to the path of travel 180.

In another aspect of the present invention, an orthodontic bracket 10 includes a base member 13 defining an archwire slot 14 and which traverses the base member 13, and wherein the archwire slot 14 defines an opening 44 within an anterior facing surface 20 of the base member 13. Still further, in the first form of the invention 10, a channel 43 extends along the anterior side 20 of the base member 13 from the archwire slot 14 to a lowermost surface 23 of the base member 13. In this arrangement, a fixed projection 34 extends laterally outwardly from the base member 13 and into a portion of the channel 43. Further, a biasing member 17 resiliently cooperates with the fixed projection 34.

The present invention also relates to a method of forming an orthodontic bracket 10 which includes providing an orthodontic bracket base member 13 having an anterior surface 20 and a posterior surface 21; providing an opening 44 within the anterior surface 20 of the base member 13, and wherein the opening 44 traverses the width of the base member 13, and further defines, at least in part, an archwire slot 14. Still further, the present methodology includes a step of providing a channel 43 within the base member 13, and which extends downwardly relative to the archwire slot 14; and providing a projection 34 extending outwardly from the channel 43 and which is rigidly affixed to the base member 13. The present methodology also relates to a method of forming an orthodontic bracket which includes the steps of providing a ligating slide 16, 106 which is moveably borne by a base member 13, 103; and coupling a biasing member 17, 107 to the ligating slide 16, 106, and wherein the biasing member is substantially parallel to the ligating slide.

Therefore, it will be seen that the present invention has been designed to meet the future needs of the orthodontic profession, and further addresses many of the shortcomings attendant with the prior art devices and practices which have been utilized heretofore. The present orthodontic bracket will result in a greater range of treatment options and the quality of the resulting orthodontic treatment will be greatly improved in view of the many features of the present invention.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. An orthodontic bracket for coupling an archwire with a tooth, comprising:
    a bracket body that is configured to be mounted to the tooth and that includes an archwire slot with a base surface and having opposed slot surfaces extending away from the base surface, an anterior surface, and a recess in the anterior surface;
    a ligating slide that includes a superior end and that is engaged with and movable relative to the bracket body between an opened position and a closed position, wherein the ligating slide opposes the base surface in the closed position;
    a resilient member that at least in part defines a channel and an edge of the channel defines an abutment; and
    a projection that cooperates with the resilient member to releasably restrain the ligating slide in the closed position,
    wherein during movement of the ligating slide, the projection is movable within the channel to slidably engage the abutment, and
    wherein the recess includes a wall that faces the superior end of the ligating slide in the closed position and the recess is configured to receive a tool to contact the superior end of the ligating slide and to move the ligating slide toward the opened position.

2. The bracket of claim 1, wherein the abutment releasably supports the ligating slide in the closed position.

3. The bracket of claim 1, wherein the abutment separates the channel into a first portion and a second portion, the first portion configured to receive the projection when the ligating slide is in the opened position and the second portion configured to receive the projection when the ligating slide is in the closed position.

4. The bracket of claim 1, wherein the abutment forms a restriction in the channel.

5. The bracket of claim 1, wherein contact between the projection and the abutment causes the resilient member to resiliently deform.

6. The bracket of claim 1, wherein a portion of one of the opposed slot surfaces opposes the superior end of the ligating slide in the closed position.

7. The bracket of claim 1, wherein the recess is narrower in width than the width of the ligating slide.

8. The bracket of claim 1, wherein the bracket body has a slide channel that includes a support surface, the slide channel opens to the archwire slot opposite the recess, and the ligating slide is slidably engaged with the support surface.

9. The bracket of claim 8, wherein the support surface carries a pair of opposed guide members that define at least a portion of the slide channel and the ligating slide is slidable between the pair of opposed guide members.

10. The bracket of claim 9, wherein each opposed guide member of the pair of opposed guide members is generally L-shaped.

11. The bracket of claim 1, wherein the resilient member forms an integral portion of the ligating slide.

12. The bracket of claim 1, wherein the resilient member is planar.

13. The bracket of claim 1, wherein the resilient member is borne by the bracket body.

14. An orthodontic bracket for coupling an archwire with a tooth comprising:
    a bracket body that is configured to be mounted to the tooth and that includes an archwire slot with a base surface and having opposed slot surfaces extending away from the base surface;
    a ligating slide that is movable relative to the bracket body between an opened position and a closed position, wherein the ligating slide opposes the base surface in the closed position;
    a resilient member that releasably restrains the ligating slide in the closed position and at least in part defines a channel and an edge of the channel defines an abutment; and
    a projection that is movable within the channel to slidably engage the abutment,
    wherein the abutment separates the channel into a first portion and a second portion, the first portion configured to receive the projection when the ligating slide is in the opened position and the second portion configured to receive the projection when the ligating slide is in the closed position.

15. The bracket of claim 14, wherein the abutment releasably supports the ligating slide in the closed position.

16. The bracket of claim 14, wherein the resilient member forms an integral portion of the ligating slide.

17. The bracket of claim 14, wherein the resilient member is planar.

18. The bracket of claim 14, wherein the resilient member is borne by the bracket body.

* * * * *